(12) United States Patent
Matsui

(10) Patent No.: US 8,233,037 B2
(45) Date of Patent: Jul. 31, 2012

(54) IMAGE DISPLAY APPARATUS

(75) Inventor: Akira Matsui, Tokyo (JP)

(73) Assignee: Olympus Corporation, Tokyo (JP)

( * ) Notice: Subject to any disclaimer, the term of this patent is extended or adjusted under 35 U.S.C. 154(b) by 1167 days.

(21) Appl. No.: 11/863,611

(22) Filed: Sep. 28, 2007

(65) Prior Publication Data

US 2008/0086028 A1    Apr. 10, 2008

(51) Int. Cl.
    *A61B 1/04*    (2006.01)
(52) U.S. Cl. .............................. 348/65; 345/77; 345/506
(58) Field of Classification Search .................... 348/65; 345/77, 506
    See application file for complete search history.

(56) References Cited

U.S. PATENT DOCUMENTS

| | | | |
|---|---|---|---|
| 3,905,132 A * | 9/1975 | Dyer | 434/323 |
| 5,144,446 A * | 9/1992 | Sudo et al. | 348/246 |
| 5,317,420 A * | 5/1994 | Kuwahara | 358/463 |
| 6,373,890 B1 * | 4/2002 | Freeman | 375/240 |
| 6,628,290 B1 * | 9/2003 | Kirk et al. | 345/506 |
| 7,120,924 B1 * | 10/2006 | Katcher et al. | 725/60 |
| 7,221,465 B1 * | 5/2007 | Shimada | 358/1.14 |
| 7,616,834 B2 * | 11/2009 | Kramer et al. | 382/276 |
| 2004/0225223 A1 * | 11/2004 | Honda et al. | 600/476 |
| 2005/0237384 A1 * | 10/2005 | Jess et al. | 348/42 |
| 2005/0283053 A1 * | 12/2005 | deCharms | 600/300 |
| 2009/0243498 A1 * | 10/2009 | Childs et al. | 315/169.3 |
| 2010/0026613 A1 * | 2/2010 | Morvan et al. | 345/77 |
| 2010/0188443 A1 * | 7/2010 | Lewis et al. | 345/691 |

FOREIGN PATENT DOCUMENTS

| | | |
|---|---|---|
| JP | HEI 05-220115 | 8/1993 |
| JP | HEI 07-271963 | 10/1995 |
| JP | 2003-19111 | 1/2003 |
| JP | 2004-337596 | 12/2004 |

OTHER PUBLICATIONS

Japanese Official Action dated Mar. 9, 2010 together with a partial English translation.

* cited by examiner

*Primary Examiner* — Wing Chan
*Assistant Examiner* — Tesfay Yohannes
(74) *Attorney, Agent, or Firm* — Scully, Scott, Murphy & Presser, P.C.

(57) ABSTRACT

Provided is an image display apparatus that includes a display unit that displays a series of images obtained by imaging an inside of a subject in time sequence, and displays a time bar indicating imaging periods of the series of images so that areas of the time bar are identified by different colors corresponding respectively to regions of the inside of the subject. The apparatus also includes a control unit that identifies the respective regions of the inside of the subject, which are displayed on the series of images, and controls the display unit so that, for each of the regions identified, an area of the time bar corresponding to a period when a series of images of the region are displayed is colored with a substitute color identifying the region.

5 Claims, 16 Drawing Sheets

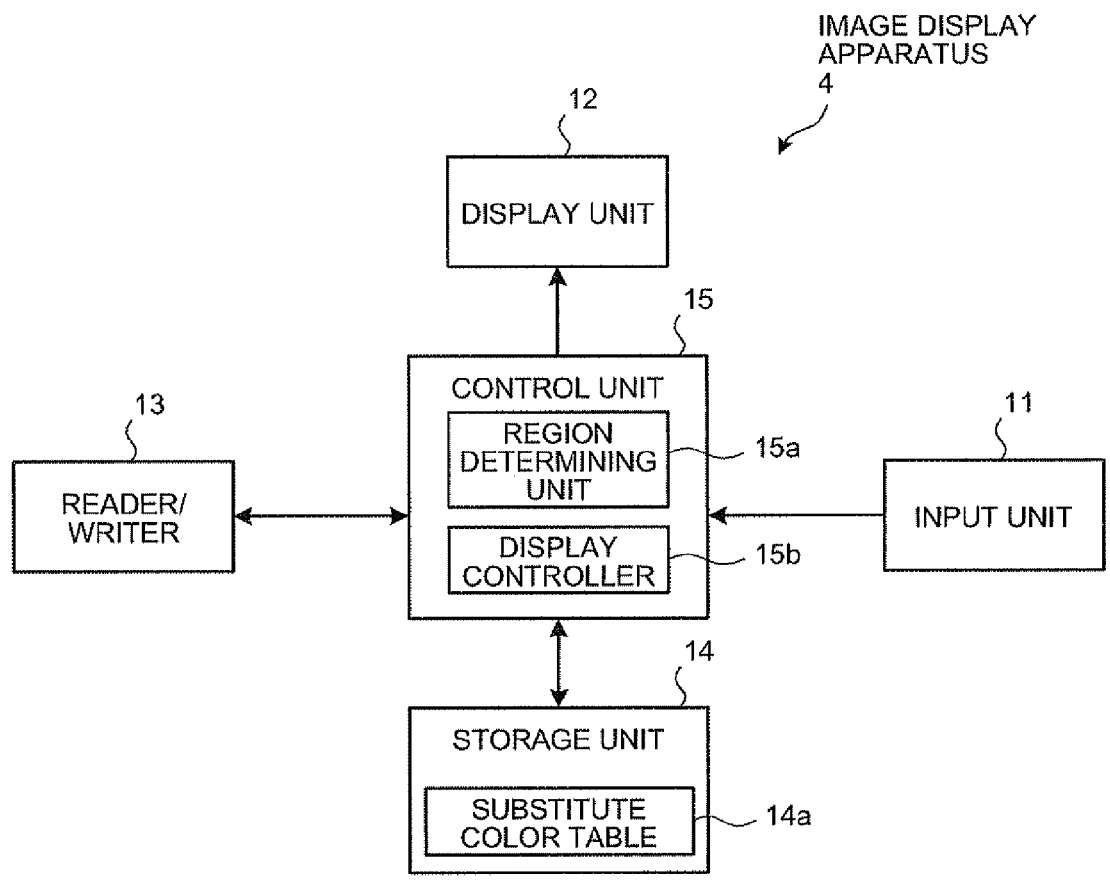

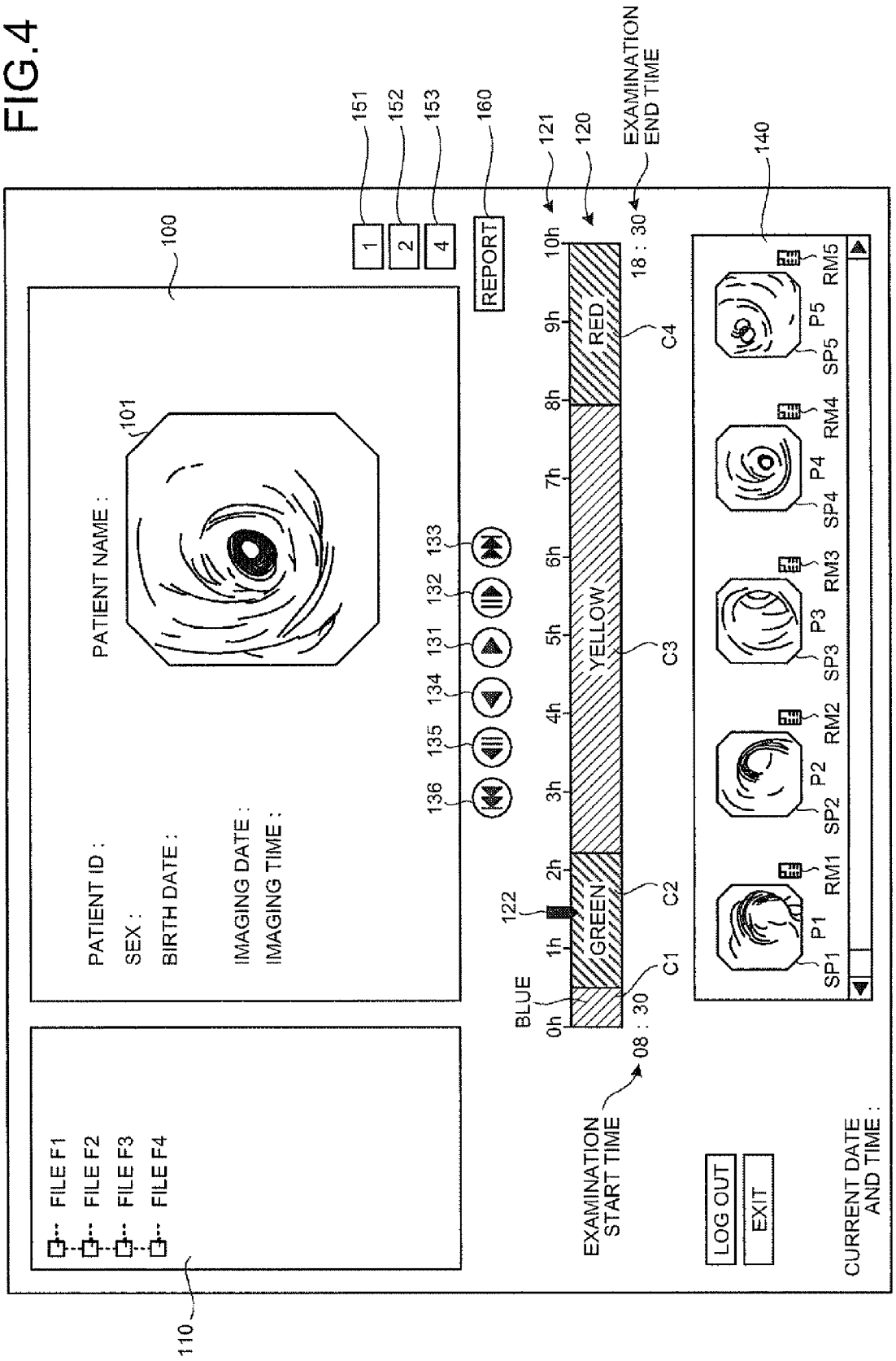

IMAGE DISPLAY APPARATUS

BACKGROUND OF THE INVENTION

1. Field of the Invention

The present invention relates to an image display apparatus that displays a series of intra-subject images, which are picked up in time sequence.

2. Description of the Related Art

In recent years, in the endoscope field, there has been proposed a swallow-type capsule endoscope provided with an imaging function and a radio communication function, and a capsule endoscope system that acquires intra-subject images using this capsule endoscope has been developed. This capsule endoscope operates so as to move through a body cavity, for example, the inside of organs such as stomach and small intestine according to its peristaltic movement and pick up intra-subject images, for example, every 0.5 second in a period after the endoscope is swallowed for observation (examination) from a mouth of a subject until it is naturally discharged.

While the capsule endoscope is moving inside of the subject, the images picked up by this capsule endoscope are sequentially transmitted to an external receiving apparatus via radio communication. The receiving apparatus has a radio communication function and a memory function, so that the images received from the capsule endoscope inside the subject are sequentially stored in a memory. The subject can freely act in the period after swallowing the capsule endoscope until naturally discharging it by carrying the receiving apparatus. After the capsule endoscope is naturally discharged from the subject, the images accumulated in the memory is loaded onto an image display apparatus by a doctor or a nurse, and the images of the organs inside the subject can be displayed on the image display apparatus to make a diagnosis for the subject (e.g., Japanese Patent Application Laid-Open No. 2003-19111).

Generally, such an image display apparatus sequentially displays a series of intra-subject images picked up by the capsule endoscope, and displays a time bar indicating an elapsed time from imaging start of the series of images. By confirming this time bar, the doctor or the nurse knows the elapsed time from the imaging start until the intra-subject image being displayed was picked up. In this case, the doctor or the nurse, based on the elapsed time, estimates a position of the capsule endoscope moving inside the subject until the intra-subject image being displayed was picked up, that is, an imaged region (organ) of the intra-subject image being displayed. Also, there is an image display apparatus that detects average colors of respective images contained in a series of intra-subject images and further displays the detected average colors of the respective images on the above-described time bar. In this case, the average colors of the intra-subject images are unique to the respective intra-subject regions, and are displayed in areas on the time bar temporally corresponding to the respective intra-subject images, so that the doctor or the nurse estimates the imaged region (organ) of the intra-subject image being displayed by visually confirming the average color displayed on the time bar.

However, the above-described conventional image display apparatus has a problem in that since the average colors of the respective intra-subject images are displayed on the time bar to color-code the time bar by the intra-subject region, in many cases, borders between the adjacent displayed colors on the time bar are unclear, which makes it difficult to know the border between the images when the intra-subject region changes (e.g., border between the images at the time of change from an image of stomach to an image of small intestine) in a series of intra-subject images, and thus makes it difficult to determine the intra-subject region whose image is displayed. This problem is remarkable in the images in temporal vicinity of the borders of the images.

SUMMARY OF THE INVENTION

An image display apparatus according to an aspect of the present invention includes a display unit that displays a series of images obtained by imaging an inside of a subject in time sequence, and displays a time bar indicating imaging periods of the series of images so that areas of the time bar are identified by different colors corresponding respectively to regions of the inside of the subject; and a control unit that identifies the respective regions of the inside of the subject, which are displayed on the series of images, and controls the display unit so that, for each of the regions identified, an area of the time bar corresponding to a period when a series of images of the region are displayed is colored with a substitute color identifying the region.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a block diagram schematically showing one configuration example of the image display apparatus, which is an embodiment of this invention;

FIG. 3 is a schematic diagram showing a specific example of a substitute color table;

FIG. 4 is a schematic diagram showing one specific example of a display screen;

DETAILED DESCRIPTION OF THE PREFERRED EMBODIMENTS

Figure 1:
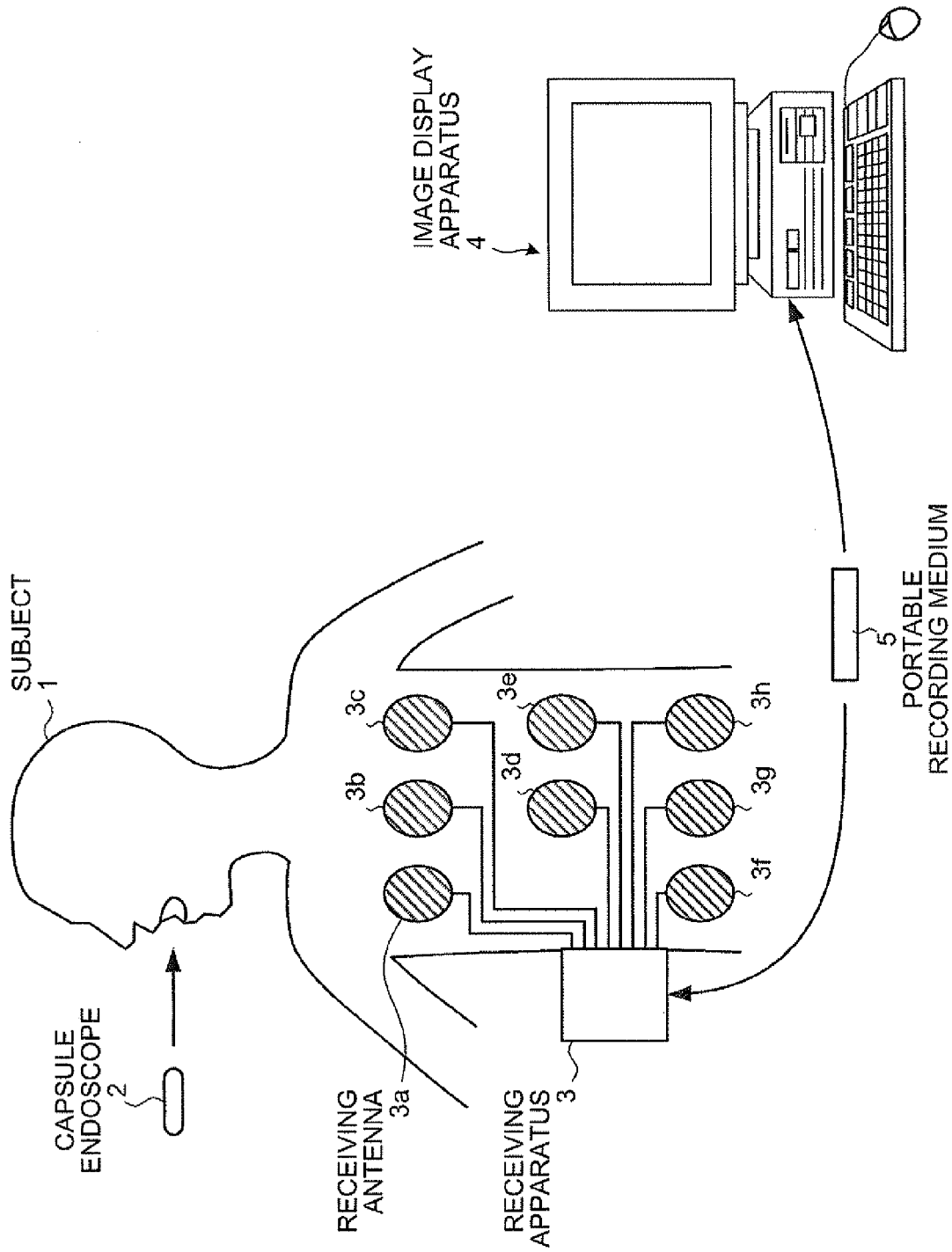
FIG. 1 is a schematic diagram illustrating one configuration example of a capsule endoscope system with an image display apparatus, which is an embodiment of this invention.

Hereinafter, referring to the drawings, preferred embodiments of an image display apparatus according to the present invention are described in detail. Although as one example of the image display apparatus according to the present invention, an image display apparatus used in a capsule endoscope system is exemplified, this does not limit the scope of the present invention.

FIG. 1 is a schematic view illustrating one configuration example of a capsule endoscope system with an image display apparatus, which is an embodiment of this invention. As shown in FIG. 1, this capsule endoscope system is provided with a capsule endoscope 2 that moves along a passage inside a subject 1 and picks up intra-subject 1 images, a receiving apparatus 3 that receives and accumulates the images radio-transmitted from the capsule endoscope 2, an image display apparatus 4 that displays the intra-subject 1 images, which the capsule endoscope 2 has picked up in time sequence, and a portable recording medium 5 for delivering and receiving information between the receiving apparatus 3 and the image display apparatus 4.

The capsule endoscope 2 has an imaging function of imaging the inside of the subject 1, and a radio communication function of transmitting the images obtained by imaging the inside of the subject 1 to the receiving apparatus 3. By being swallowing by the subject 1, the capsule endoscope 2 passes through esophagus inside the subject 1, and advances through the body cavity by peristalsis of gut lumen. At the same time, the capsule endoscope 2 sequentially picks up intra-subject 1 images at predetermined intervals, for example, at 0.5 second intervals, and sequentially transmits the obtained intra-subject 1 images to the receiving apparatus 3.

The receiving apparatus 3, having receiving antennas 3a to 3h connected, performs radio communication with the capsule endoscope 2 using the receiving antennas 3a to 3h. More specifically, the receiving apparatus 3 receives a radio signal from the capsule endoscope 2 through any of the receiving antennas 3a to 3h, and acquires an intra-subject 1 image based on the received radio signal. Moreover, in the receiving apparatus 3, the portable recording medium 5 is detachably attached, and the intra-subject 1 images, which have been sequentially acquired from the capsule endoscope 2, are sequentially stored in the portable recording medium 5.

The receiving antennas 3a to 3h are realized by using, for example, loop antennas to receive the radio signal transmitted from the capsule endoscope 2. The receiving antennas 3a to 3h are arranged in predetermined positions on a body surface of the subject 1, for example, in positions corresponding to the passage of the capsule endoscope 2, as shown in FIG. 1. The receiving antennas 3a to 3h may be arranged in predetermined positions of a jacket worn by the subject 1. In this case, the subject 1 wears the jacket, by which the receiving antennas 3a to 3h are arranged in the predetermined positions on the body surface of the subject 1 corresponding to the passage of the capsule endoscope 2. Moreover, in the subject 1, it is only required to arrange a plurality of receiving antennas on the subject 1. In this case, the number of the arranged receiving antennas is not particularly limited to eight.

The portable recording medium 5 is a portable recording medium such as CompactFlash®. The portable recording medium 5 is detachable from the receiving apparatus 3 and the image display apparatus 4, and has a structure capable of outputting and recording information at the time of the attachment to both. More specifically, when attached to the receiving apparatus 3, the portable recording medium 5 sequentially stores data such as the images that the receiving apparatus 3 has acquired from the capsule endoscope 2. Also, when the portable recording medium 5 is attached to the image display apparatus 4, the data such as the stored images is loaded on the image display apparatus 4, or information of the subject 1 and the like are written by the image display apparatus 4.

The image display apparatus 4 is intended to display the images picked up by the capsule endoscope 2, and the like, has such a configuration as a workstation displaying the intra-subject 1 images acquired through the portable recording medium 5. In this case, the image display apparatus 4 has a processing function for an examiner such as a doctor or a nurse to observe the intra-subject 1 images and make a diagnosis for the subject 1. The examiner causes the image display apparatus 4 to sequentially display the intra-subject 1 images to observe (examine) intra-subject 1 regions, for example, esophagus, stomach, small intestine, large intestine and the like, which enables diagnosis for the subject 1.

FIG. 2 is a block diagram schematically showing one configuration example of the image display apparatus 4. As shown in FIG. 2, the image display apparatus 4 has an input unit 11 that inputs various types of information for displaying and observing the intra-subject 1 images, a display unit 12 that screen-displays the various types of information for observing (examining) the inside of the subject 1 on the intra-subject 1 images to make a diagnosis, and a reader/writer 13 that loads the data such as the images accumulated in the portable recording medium 5. Also, the image display apparatus 4 has a storage unit 14 that accumulates various types of data necessary for observation and diagnosis of the inside of the subject 1 on the intra-subject 1 images and the like, and a control unit 15 that performs drive control over the components of the image display apparatus 4.

The input unit 11 is realized using a keyboard, a mouth or the like, and information of commands to the control unit 15 or information of the subject 1 are input to the control unit 15 through input operation by the examiner. In this case, the input unit 11 inputs to the control unit 15, for example, the command information to display the intra-subject 1 images on the display unit 12, and the information of the subject 1 such as a name of the subject 1 (patient name), sex, birth date, patient ID and the like.

The display unit 12 is realized using a display such as a CRT display and a liquid crystal display, and displays various types of information commanded to display by the control unit 15. In this case, the display unit 12 displays, for example, the series of intra-subject 1 images picked up by the capsule endoscope 2, and the information of the subject 1. Moreover, the display unit 12 displays a time bar indicating imaging periods of the series of intra-subject 1 images. In this case, the display unit 12 color-codes and displays the time bar by the intra-subject 1 region. Detailed description of specific examples of display screen by the display unit 12 will be given later.

The reader/writer 13 has the above-described portable recording medium 5 attached detachably, and loads the data accumulated in the attached portable recording medium 5, for example, the series of intra-subject 1 images, and transfers the loaded data to the control unit 15. Moreover, the reader/writer 13 writes, on the attached portable recording medium 5, information commanded to write by the control unit 15, for example, the information of the subject 1.

The storage unit 14 accumulates the information commanded to write by the control unit 15, for example, the series of intra-subject 1 intra-subject 1 images, the information of the subject 1 and the like. Moreover, the storage unit 14 reads the accumulated information commanded to read by the control unit 15, and transfers the same to the control unit 15. The storage unit 14 may be configured so as to accumulate the various types of information in itself using information recording means, capable of accumulating and reading the information, such as RAM, EEPROM, hard disk and the like, or may be configured such that a portable recording medium such as CD and DVD is attached detachably and that the information is accumulated in the attached CD, DVD or the like.

Moreover, the storage unit 14 has a substitute color table 14*a* for color-coding the time bar displayed on the display unit 12 by the intra-subject 1 region. FIG. 3 is a schematic diagram showing one specific example of the substitute color table 14*a*. As shown in FIG. 3, in the substitute color table 14*a*, each of the intra-subject 1 observation regions to be imaged and displayed on the display unit 12 and be observed (e.g., esophagus, stomach, small intestine, and large intestine) and the substitute color corresponding to the relevant intra-subject 1 observation region are associated with each other. In this case, in the substitute color table 14*a*, for example, esophagus and a substitute color (blue) are associated, stomach and a substitute color (green) are associated, small intestine and a substitute color (yellow) are associated, and large intestine and a substitute color (red) are associated. These substitute colors substitute for average colors of the respective images obtained by imaging the respective intra-subject 1 observation regions, and differ in each intra-subject 1 observation region. Moreover, the combination of the observation regions and the substitute colors is not limited to the illustrated ones in the substitute color table 14*a* of FIG. 3.

As the substitute colors, those having enough contrast to form a border between adjacent different substitute colors when displayed on a time bar 120, for example, those having differences in hue, lightness, and saturation of predetermined values or higher are used. More specifically, desired colors selected from seven spectral colors of red, orange, yellow, green, blue, indigo and violet, for example, are used. In this case, the respective substitute colors of the adjacent observation regions, for example, substitute colors of esophagus and stomach, substitute colors of stomach and small intestine, substitute colors of small intestine and large intestine are desirably ones whose color systems are far from each other, respectively.

The control unit 15, as described above, performs the drive control over the respective components of the image display apparatus 4, for example, the input unit 11, the display unit 12, the reader/writer 13, and the storage unit 14, and performs the input and output control of information over the respective components and information processing for inputting and outputting various types of information between the respective components. Moreover, when the control unit 15 loads the series of images from the portable recording medium 5, each of the images contained in the series of images is associated with an imaging time and is filed, and the file containing the series of images is stored in the storage unit 14 to be retained and managed. In this case, the control unit 15 may associate each of the images with an elapsed time after the capsule endoscope 2 starts imaging until it picks up the relevant image instead of the imaging time of the relevant image.

Moreover, the control unit 15 has a region determining unit 15*a* and a display controller 15*b*. The region determining unit 15*a* detects color information, for example, an average color of each of the images contained in the series of images, and determines the intra-subject 1 observation region displayed on the relevant image, based on the detected average color of the image. The display controller 15*b* performs control over the display unit 12 so as to display various types of information. In this case, the display controller 15*b*, for example, causes the display unit 12 to display the information for observing the inside of the subject 1 on the series of intra-subject 1 images and the like, and making a diagnosis. Moreover, the display controller 15*b* refer to the substitute color table 14*a*, color-codes the above-described time bar by the observation region determined by the region determining unit 15*a* and causes the display unit 12 to display it.

Next, the display screen displayed by the display unit 12 is described in detail. FIG. 4 is a schematic diagram showing one specific example of the display screen of the display unit 12. As shown in FIG. 4, on the display screen of the display unit 12, there are formed a main-image display area 100 where the images of the intra-subject 1 observation region are displayed, a file display area 110 where a list of files each containing the series of images picked up by the capsule endoscope 2 is displayed, the time bar 120 indicating the imaging periods of the series of images displayed in the main-image display area 100, and display operation icons 131 to 136 for performing operations to display the images of the observation regions in the main-image display area 100. Also, on the display screen of the display unit 12, there are formed a subimage display area 140 that additionally displays desired images selected from the images displayed in the main-image display area 100 as thumbnail images, number setting icons 151 to 153 that each set the number of images to be simultaneously displayed in the main-image display area 100, and a report icon 160 for creating a report such as findings to the observation region or the like.

In the main-image display area 100, a series of images contained in a file selected from the respective files, the list of which is displayed in the file display area 110, for example, files F1 to F4, are displayed. More specifically, if the number setting icon 151, which sets the number of images to be simultaneously displayed in the main-image display area 100 to one, is selected by the operation of the input unit 11, each of the images contained in the series of images, for example, an image 101 is displayed one by one in the main image display area 100. In this case, if any one of the display operation icons 131 to 133 is selected by the operation of the input unit 11, the series of images are sequentially displayed forward in time sequence in the main-image display area 100. On the other hand, if any one of the display operation icons 134 to 136 is selected by the operation of the input unit 11, the series of images are sequentially displayed backward in time sequence in the main-image display area 100. If the display operation icons 131, 134 are selected, the series of images are sequentially displayed at a standard display frame rate in the main-image display area 100; if the display operation icons 132, 135 are selected, one frame is displayed every time the icon is selected (reproduce the next frame); and if the display operation icons 133, 136 are selected, the images are sequentially displayed at a fast display frame rate as compared with the standard display frame rate. Furthermore, in the main-image display area 100, as shown in FIG. 4, the information of the subject 1 to be imaged and displayed, for example, a patient name, patient ID, sex, and birth date are displayed, and an imaging date and an imaging time of the image 101 being displayed among the series of intra-subject 1 images are displayed.

The time bar 120 is provided with a time scale 121 indicating an elapsed time from a time point when the capsule endoscope 2 starts imaging the inside of the subject 1 as a time scale which indicates the imaging period of the series of the intra-subject 1 images displayed in the main image display area 100. In this case, a maximum value of the elapsed time indicated by the time scale 121 is fixed to a predetermined time, for example, 10 hours. The elapsed time indicated by the time scale 121 corresponds to an elapsed time from a time point when the capsule endoscope 2 is introduced into the subject 1 and the examination of the subject 1 starts. Moreover, the time bar 120 has a display position marker 122 moving forward or backward in time sequence along the time scale 121. The display position marker 122 is formed on the time bar 121 as an index indicating the elapsed time from the examination start of the images displayed in the main-image display area 100, and moves forward or backward in time sequence along the time scale 121 in sync with switching of the images displayed in the main-image display area 100. In this case, the display position marker 122 moves so as to indicate a position on the time scale 121 temporally corresponding to the imaging time of the image being displayed in the main-image display area 100. On the time bar 120, an imaging start time of the series of intra-subject 1 images, that is, examination start time of the subject 1 (e.g., 08:30) is displayed in the vicinity of a left end, which indicates that the elapsed time indicated by the time scale 121 is 0 hour (0 h), while an examination end time of the subject 1 (e.g., 18:30) is displayed in the vicinity of a right end, which corresponds to the maximum value of the elapsed timer for example, 10 hours (10 h).

Moreover, as shown in FIG. 4, for example, the time bar 120 is color-coded by substitute colors C1 to C4 corresponding to the respective intra-subject 1 observation regions (esophagus, stomach, small intestine, and large intestine), respectively. More specifically, on the time bar 120, the blue substitute color C1 is displayed in an area on the time bar 120 temporally corresponding to one or more images obtained by imaging esophagus of the subject 1, the green substitute color C2 is displayed in an area on the time bar 120 temporally corresponding to one or more images obtained by imaging stomach of the subject 1, the yellow substitute color C3 is displayed in an area on the time bar 120 temporally corresponding to one or more images obtained by imaging small intestine of the subject 1, and the red substitute color C4 is displayed in an area on the time bar 120 temporally corresponding to one or more images obtained by imaging large intestine of the subject 1. The action of color-coding the time bar 120 by the substitute colors will be described later.

As for the subimage display area 140, if the examiner operates the input unit 11 to select a desired image in the main-image display area 100, a thumbnail image corresponding to this desired image is additionally displayed. In this case, as shown in FIG. 4, for example, thumbnail images SP1 to SP5 are additionally displayed in the subimage display area 140. Selecting any one of the thumbnail images SP1 to SP5 allows an image corresponding to the selected thumbnail image to be displayed in the main-image display area 100. Moreover, a desired comment can be appended to each of the thumbnail images in the subimage display area 140. More specifically, to the thumbnail images SP1 to SP5 are appended comments P1 to P5 indicating names of imaged organs (e.g., duodenum, jejunum, small intestine or the like) or desired comments specifying the thumbnail images (e.g., bleeding site, lesion or the like), respectively. Furthermore, if the report icon 160 is selected to create a report such as findings for the observation region, a report mark indicating that the report has been created (appended) is given to the thumbnail image corresponding to the image obtained by imaging this observation region. More specifically, for example, if a report is created for each of the images corresponding to the thumbnail images SP1 to SP5, as shown in FIG. 4, report marks RM1 to RM5 are given to the thumbnail images SP1 to SP5, respectively. In this case, by operating the input unit 11 to select the desired report mark, the examiner can view the report corresponding to the selected report mark.

Figure 5:
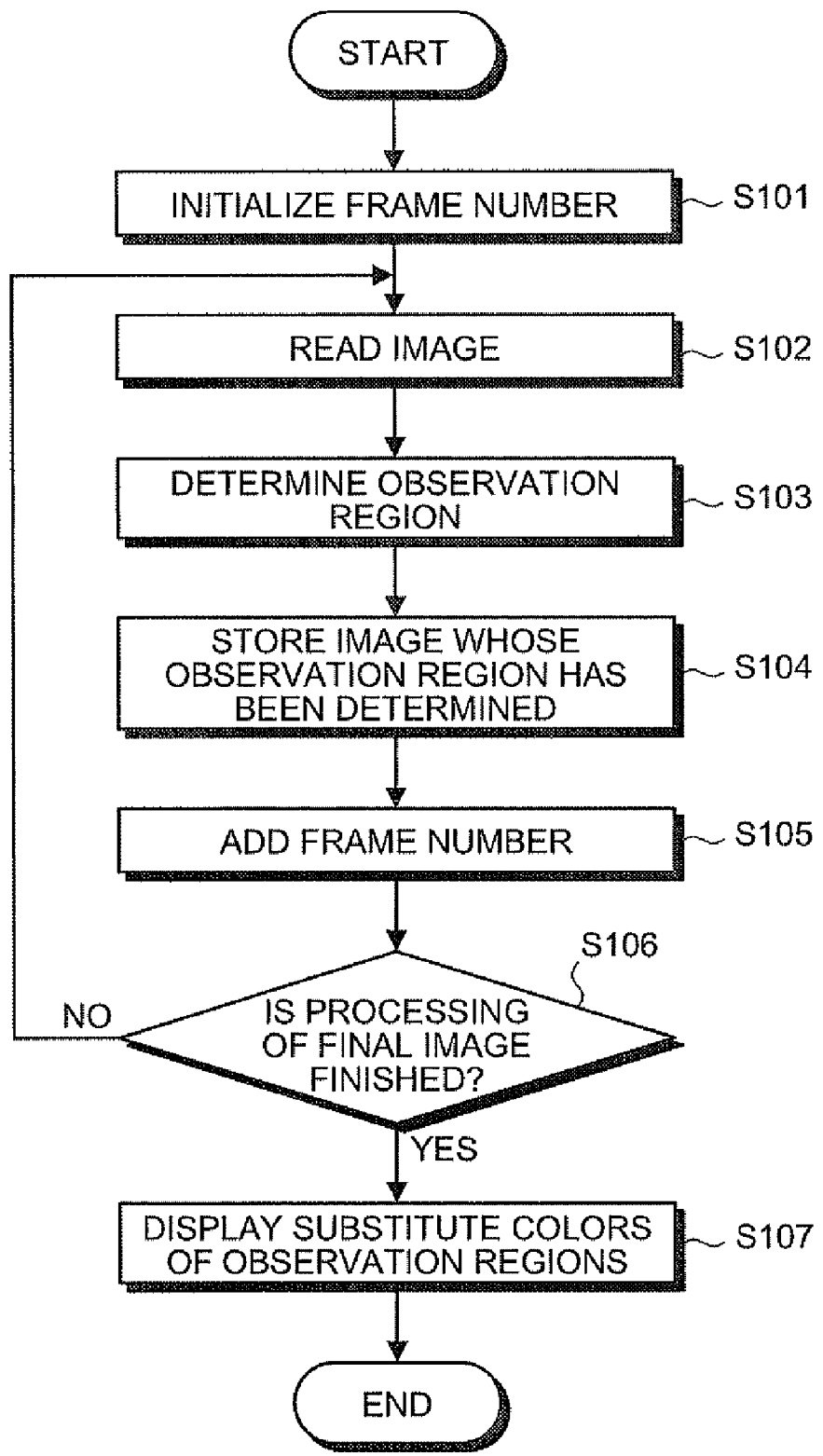
FIG. 5 is a flowchart for explaining processing steps until a time bar is color-coded by observation region determined based on an average color.

Next, the action of color-coding the time bar 120 by the observation region using the above-described substitute colors is described in detail. FIG. 5 is a flowchart for explaining processing steps until the control unit 15 color-codes the time bar 120 by the observation region. When a desired file to be displayed is selected from the files F1 to F4, for example, in the file display area 110, the respective observation regions displayed on a series of images contained in the desired file are determined, and the time bar 120 is color-coded by the substitute colors corresponding to the observation regions, respectively. Namely, in FIG. 5, the control unit 15 first initializes a frame number of an image to be read as a processing object (step S101), for example, sets frame number n=1. In this case, the control unit 15 will read a leading image of the series of images to be displayed as the processing object in time sequence. Thereafter, the control unit 15 reads the image to be processed, for example, the leading image of the series of images from the storage unit 14 (step S102).

When the image to be processed is read, the control unit 15 determines the intra-subject 1 observation region displayed on the image to be processed (step S103). In this case, the region determining unit 15*a* detects color information of the image to be processed which has been read in step S102, for example, the average color, and determines the observation region of the image to be processed, based on the detected average color. For example, if the average color of the image to be processed is pale, the region determining unit 15*a* determines that the observation region displayed on the image to be processed is esophagus, and if the average color of the image to be processed is red, the region determining unit 15*a* determines that the observation region displayed on the image to be processed is stomach. Moreover, if the average color of the image to be processed is yellow, the region determining unit 15*a* determines that the observation region displayed on the image to be processed is small intestine, and if the average color of the image to be processed is orange, the region determining unit 15*a* determines that the observation region displayed on the image to be processed is large intestine.

The region determining unit 15*a* may determine the observation region on the processing image based on respective values of color elements forming the average color of the image to be processed, for example, a red color element R, a green color element G, and a blue color element B. More specifically, if the respective values of the color elements R, G, B are within a range of numeric values of the color elements forming the average color of esophagus, the region determining unit 15a may determine that the observation region on the image to be processed is esophagus, if the respective values of the color elements R, G, B are within a range of numeric values of the color elements forming the average color of stomach, the region determining unit 15a may determine that the observation region on the image to be processed is stomach, if the respective values of the color elements R, G, B are within a range of numeric values of the color elements forming the average color of small intestine, the region determining unit 15a may determine that the observation region on the image to be processed is small intestine, and if the respective values of the color elements R, G, B are within a range of numeric values of the color elements forming the average color of large intestine, the region determining unit 15a may determine that the observation region on the image to be processed is large intestine.

Next, the control unit 15 associates the image to be processed, whose observation region has been determined in step S103, with this observation region, and stores the same in the storage unit 14 (step S104). Thereby, the control unit 15 retains and manages the image to be processed as the image of the observation region determined in step S103. Then, the control unit 15 adds (+1) to the frame number n of the image (step S105). Thus, when reading an image to be processed next, the control unit 15 will read a subsequent image of the processed image, that is, an image whose frame number is n+1 in time sequence.

Thereafter, the control unit 15 determines whether or not the above-described processing from step S102 to step S105 has been completed for a final image of the series of images to be displayed, that is, an end image in time sequence (step S106). In this case, if, for example, the frame number n+1 calculated in step S105 exceeds the frame number of the images contained in the series of images to be displayed, the control unit 15 determines that the above-described processing of the step S102 and later has been completed for the final image of this series of images. If the control unit 15 determines that the processing of the final image has not been completed (step S106, No), then the above-described processing steps of step S102 and later are repeated. Namely, the controller 15 determines the observation regions with respect to the respective images contained in the series of images to be displayed, respectively, and associates the images with the determined observation regions respectively to store them in the storage unit 14.

On the other hand, if the control unit 15 determines that the processing of the final image has been completed in step S106 (step S106, Yes), the control unit 15 reads the series of images to be displayed, whose observation regions have been determined, and performs control over the display unit 12 so as to display the substitute colors corresponding to the observation regions of the respective images contained in the series of images on the time bar 120 (step S107). In this case, the display controller 15b decides the substitute colors corresponding to the observation regions of the respective images contained in the series of images, referring to the substitute color table 14a of the storage unit 14. Next, the display controller 15b performs control over the display unit 12 so as to display the substitute colors corresponding to the observation regions of the respective images in areas on the time bar 120 temporally corresponding to the respective images. In this case, the display unit 12 displays the time bar 120 color-coded by the observation region using the substitute colors.

Figure 6:
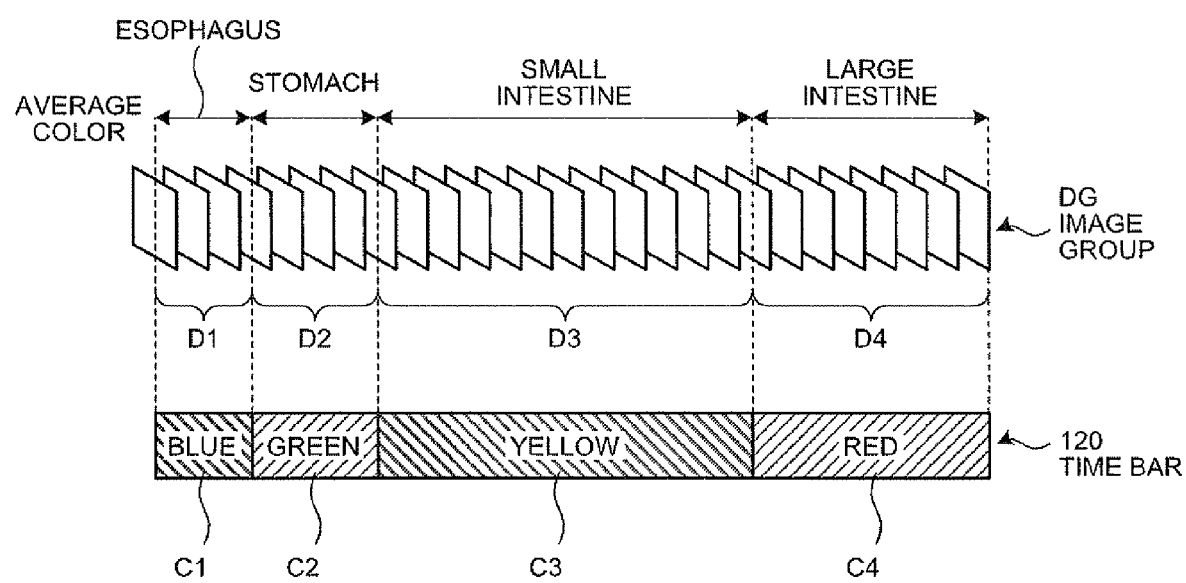
FIG. 6 is a schematic diagram for specifically explaining the action of determining observation regions of respective images and color-coding the time bar by the observation region.

FIG. 6 is a schematic diagram for specifically explaining the action in which the control unit 15 determines the observation regions of the respective images and color-codes the time bar 120 by the observation region. As shown in FIG. 6, the control unit 15 determines the observation regions of the respective images contained in an image group DG, which is a series of images to be displayed. More specifically, in the above-described step S103, the region determining unit 15a detects the average colors of the respective images of the image group DG and determines the observation regions of the respective images, based on the detected average colors. This allows the image group DG to be classified into the respective intra-subject 1 observation regions, for example, into an image group D1 on which esophagus is imaged, an image group D2 on which stomach is imaged, an image group D3 on which small intestine is imaged, and an image group D4 on which large intestine is imaged.

Moreover, the control unit 15 color-codes the time bar 120 by the observation region of the image group DG determined in the above-described step S103. In this case, the display controller 15b decides the substitute colors corresponding to the respective observation regions, referring to the substitute color table 14a of the storage unit 14, and performs the control over the display unit 12 so as to display the blue substitute color C1 corresponding to esophagus in the area on the time bar 120 temporally corresponding to the image group D1, to display the green substitute color C2 corresponding to stomach in the area on the time bar 120 temporally corresponding to the image group D2, to display the yellow substitute color C3 corresponding to small intestine in the area on the time bar 120 temporally corresponding to the image group D3, and to display the red substitute color C corresponding to large intestine in the area on the time bar 120 temporally corresponding to the image group D4. In this case, the display unit 12 displays the time bar 120 color-coded by the observation region using the substitute colors C1 to C4, as shown in FIG. 4, for example.

Here, with the substitute colors C1 to C4, the substitute color C1 corresponding to esophagus and the substitute color C2 corresponding to stomach are displayed so as to be color systems far from each other, this substitute color C2 and the substitute color C3 corresponding to small intestine are displayed so as to be color systems far from each other, and this substitute color C3 and the substitute color C4 corresponding to large intestine are displayed so as to be color systems far from each other. Thereby, the time bar 120 is clearly color-coded in a state where respective borders of the substitute colors adjacent to each other C1 to C4, that is, a border between the substitute colors C1, C2, a border between the substitute colors C2, C3, and a border between the substitute colors C3, C4 are displayed to a visible extent. The respective borders of the substitute colors C1 to C4 indicate the borders of the images when the observation region of the image group DG to be displayed changes, that is, a border between the image groups D1, D2, a border between the image groups D2, D3, and a border between the image groups D3, D4. Thus, the time bar 120 indicates the observation region of the image being displayed in the main-image display area 100 by indicating any one of the substitute colors C1 to C4 using the display position marker 122, and by causing the display position marker 122 to pass the respective borders of the substitute colors C1 to C4, the time bar 120 can indicate that the observation region of the image being displayed in the main-image display area 100 changes into a different one from the observation region of the image displayed immediately before.

By visually confirming the position on the time scale 121 indicated by the display position marker 122, the examiner knows the elapsed time from the examination start of the image in the main-image display area 100, and at the same time, by visually confirming the substitute color on the time bar 120 indicated by this display position marker 122, the examiner easily knows the observation region of the image in this main-image display area 100. Moreover, by visually confirming whether or not the display position marker 122 has passed the border of the substitute colors on the time bar 120, the examiner can easily determine whether or not the observation region of the image in the main-image display area 100 has changed from the observation region of the image displayed immediately before. For example, when the display position marker 122 has passed the border between the substitute colors C1, C2 forward in time sequence, the examiner can determine that the observation region of the image in the main-image display area 100 has changed from esophagus to stomach.

Figure 7:
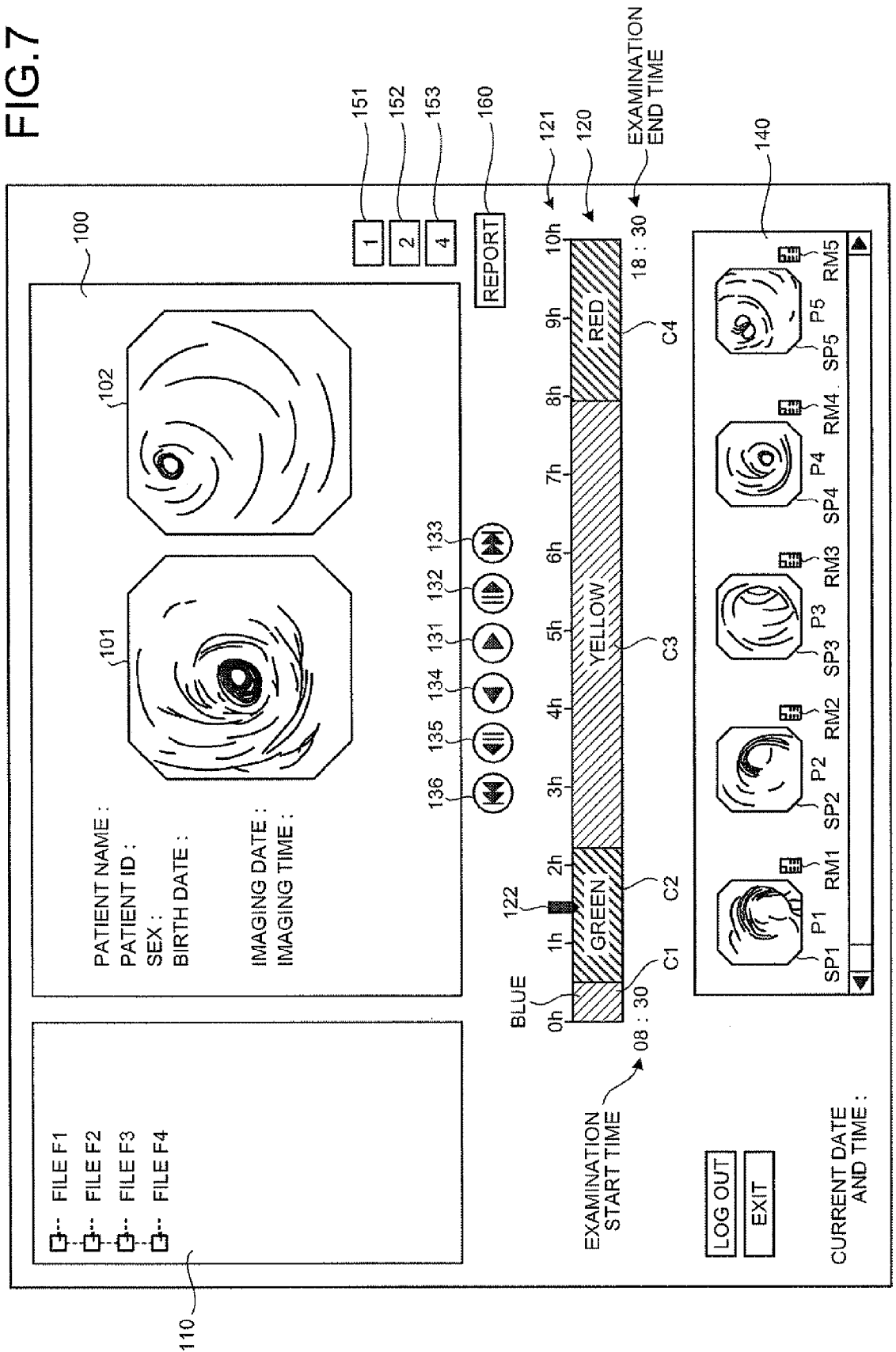
FIG. 7 is a schematic diagram showing one specific example of a display screen in the case where two images are simultaneously displayed.

Next, the action in which the display unit 12 simultaneously displays a plurality of images in the main-image display area 100 is described. FIG. 7 is a schematic diagram showing one specific example of the display screen of the display unit 12 in the case where two images are simultaneously displayed in the main-image display area 100. If the number setting icon 152 is selected by the operation of the input unit 11, the display controller 15b performs control over the display unit 12 so as to simultaneously display images contained in a series of images to be displayed two by two in the main-image display area 100. In this case, the display unit 12 will simultaneously display two images 101, 102 in the main-image display area 100, as shown in FIG. 7. The display controller 15b causes the display unit 12 to sequentially switch and display the series of images to be displayed two by two in such a switching order as to maintain a state where the images 101, 102 are continuous in time sequence, for example. This can shorten time required until the display of the series of images to be displayed is finished.

Figure 8:
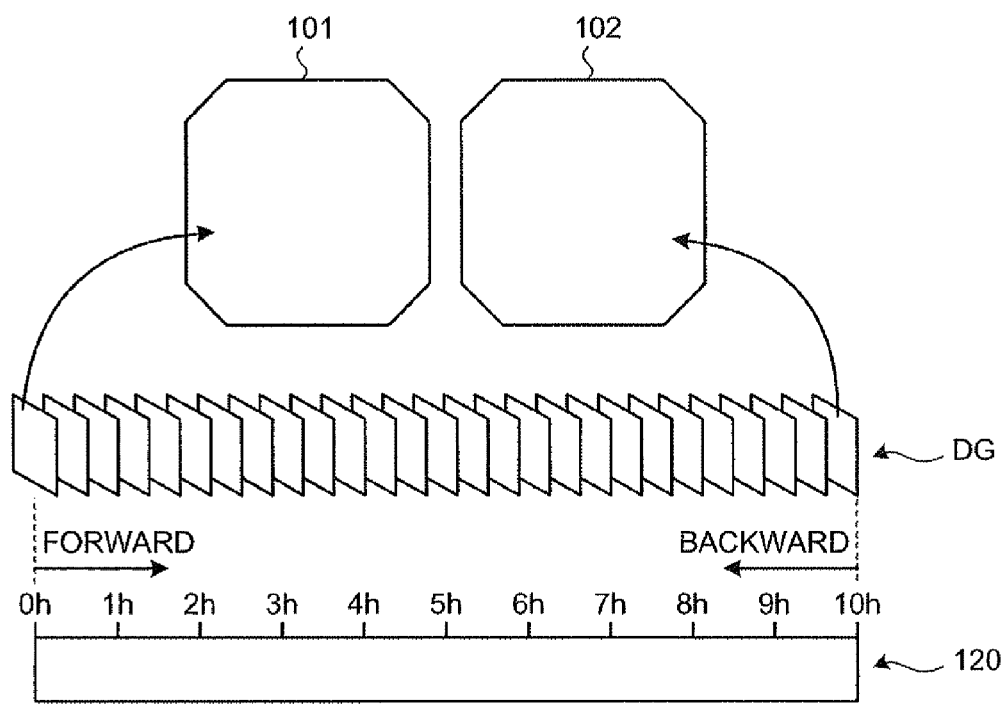
FIG. 8 is a schematic diagram for explaining the action for sequentially switching and displaying the two images in another switching order 1.

When the two images 101, 102 are simultaneously displayed in the main-image display area 100, the images 101, 102 may be discontinuous in time sequence in the series of images to be displayed. Namely, the display controller 15b may perform control over the display unit 12 so as to sequentially switch and display the series of images to be displayed two by two in a different display order from the foregoing. FIG. 8 is a schematic diagram for explaining the action for sequentially switching and displaying the two images 101, 102 in another switching order 1. As shown in FIG. 8, the display controller 15b performs control over the display unit 12 so as to sequentially switch and display the image group DG to be displayed from the leading image forward in time sequence, and in sync with this, performs control so as to sequentially switch and display the image group DG to be displayed from the last image backward in time sequence. The control of the display controller 15b in the switching order 1 allows the display unit 12 to sequentially display each of the images of the image group DG, which is sequentially switched forward, as the image 101, and to sequentially display each of the images of the image group DG, which is sequentially switched backward in time sequence, as the image 102.

Figure 9:
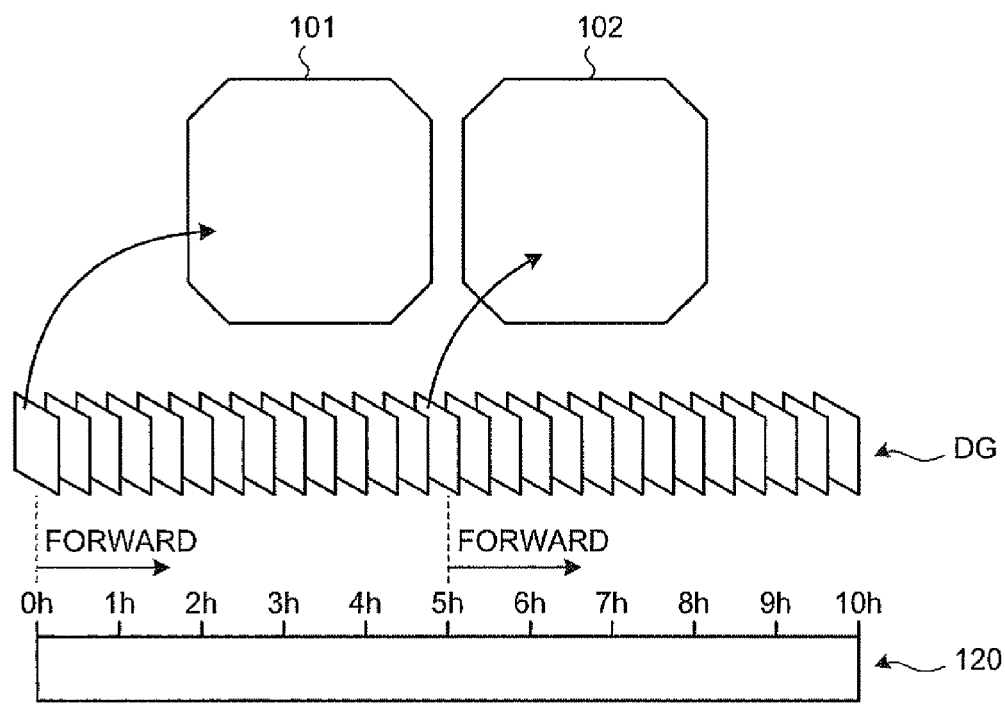
FIG. 9 is a schematic diagram for explaining the action for sequentially switching and displaying the two images in another switching order 2.

FIG. 9 is a schematic diagram for explaining the action for sequentially switching and displaying the two images 101, 102 in another switching order 2. As shown in FIG. 9, the display controller 15b may perform control over the display unit 12 so as to sequentially switch and display the image group DG to be displayed from the leading image forward in time sequence, and in sync with this, may perform control so as to sequentially switch and display the image group DG to be displayed from an intermediate image, for example, an image temporally corresponding to the vicinity of the center of the time bar 120 forward in time sequence. The control of the display controller 15b in the switching order 2 allows the display unit 12 to sequentially display each of the images of the image group DG, which is sequentially switched from the leading image forward in time sequence, as the image 101, and to sequentially display each of the images of the image group DG, which is sequentially switched from the intermediate image forward in time sequence, as the image 102.

Figure 10:
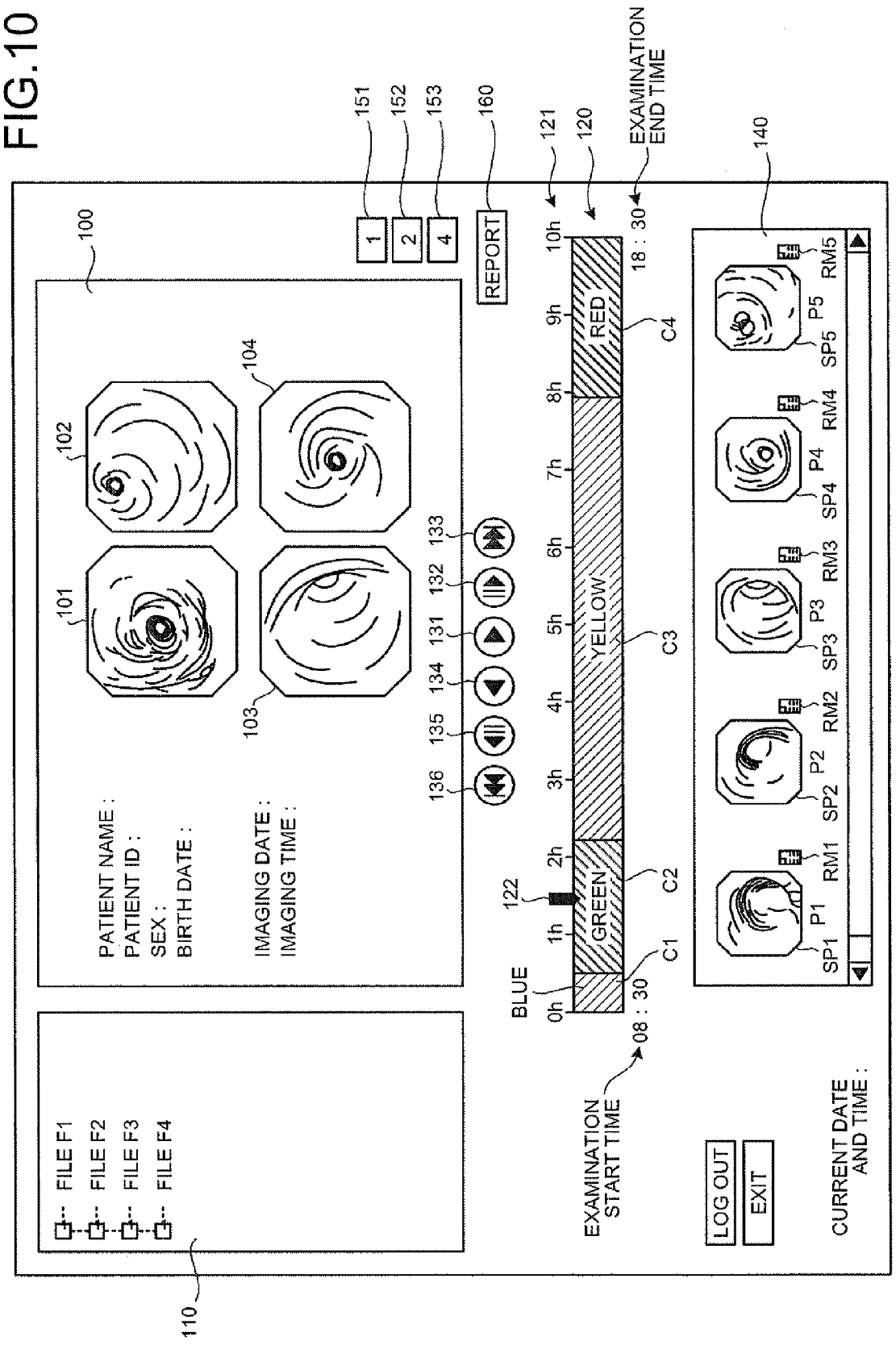
FIG. 10 is a schematic diagram showing one specific example of a display screen in the case where four images are simultaneously displayed.

On the other hand, if the number setting icon 153 is selected by the operation of the input unit 11, the display controller 15b performs control over the display unit 12 so as to simultaneously display the respective images contained in the series of images to be displayed four by four in the main-image display area 100. In this case, the display controller 15b causes the display unit 12 to sequentially switch and display the series of images to be displayed four by four in such a manner as to maintain a state where the four images are continuous in time sequence. FIG. 10 is a schematic diagram showing one specific example of the display screen of the display unit 12 in the case where four images are simultaneously displayed in the main-image display area 100. This control of the display controller 15b allows the four images 101 to 104 continuous in time sequence to be simultaneously displayed in the main-image display area 100, as shown in FIG. 10. This can further shorten time required until the display of the series of images to be displayed is finished as compared with the above-described case of two pieces.

Figure 11:
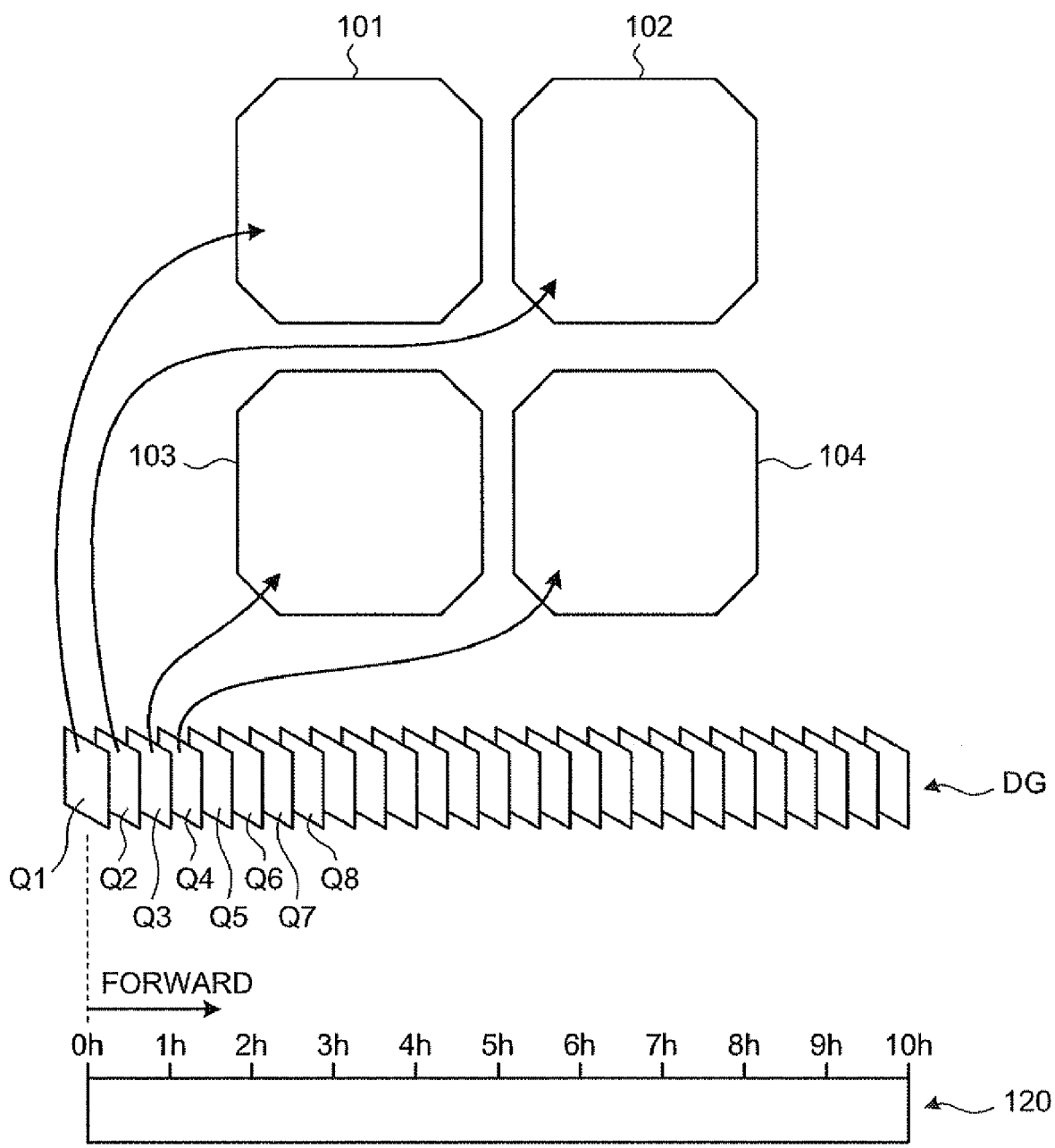
FIG. 11 is a schematic diagram for explaining the action for sequentially switching and displaying the four images in a predetermined switching order.

In this case, the display controller 15b performs the control over the display unit 12 so as to sequentially switch and display the series of images to be displayed, for example, the image group DG four by four in a predetermined switching order. FIG. 11 is a schematic diagram for explaining the action for sequentially switching and displaying the four images 101 to 104 in the predetermined switching order.

As shown in FIG. 11, the display controller 15b first performs control over the display unit 12 so as to display a leading image Q1 of the image group DG as the image 101, and display images Q2 to Q4 sequentially following the leading image Q1 forward in time sequence as the images 102 to 104, respectively. Next, when the display controller 15b causes the display unit 12 to display images Q5 to Q8 sequentially following the image Q4, the display controller 15b performs control over the display unit 12 so as to switch the images Q1 to Q4 being displayed to the images Q5 to Q8 as the images 101 to 104, respectively, and to display them. Then, the display controller 15b repeats the switching processing of the image display for the remaining image group sequentially following the image Q8. This allows the display unit 12 to sequentially switch and display the image group DG four by four so that the four continuous images of the image group DC are arrayed in the order of the images 101 to 104.

Figure 12:
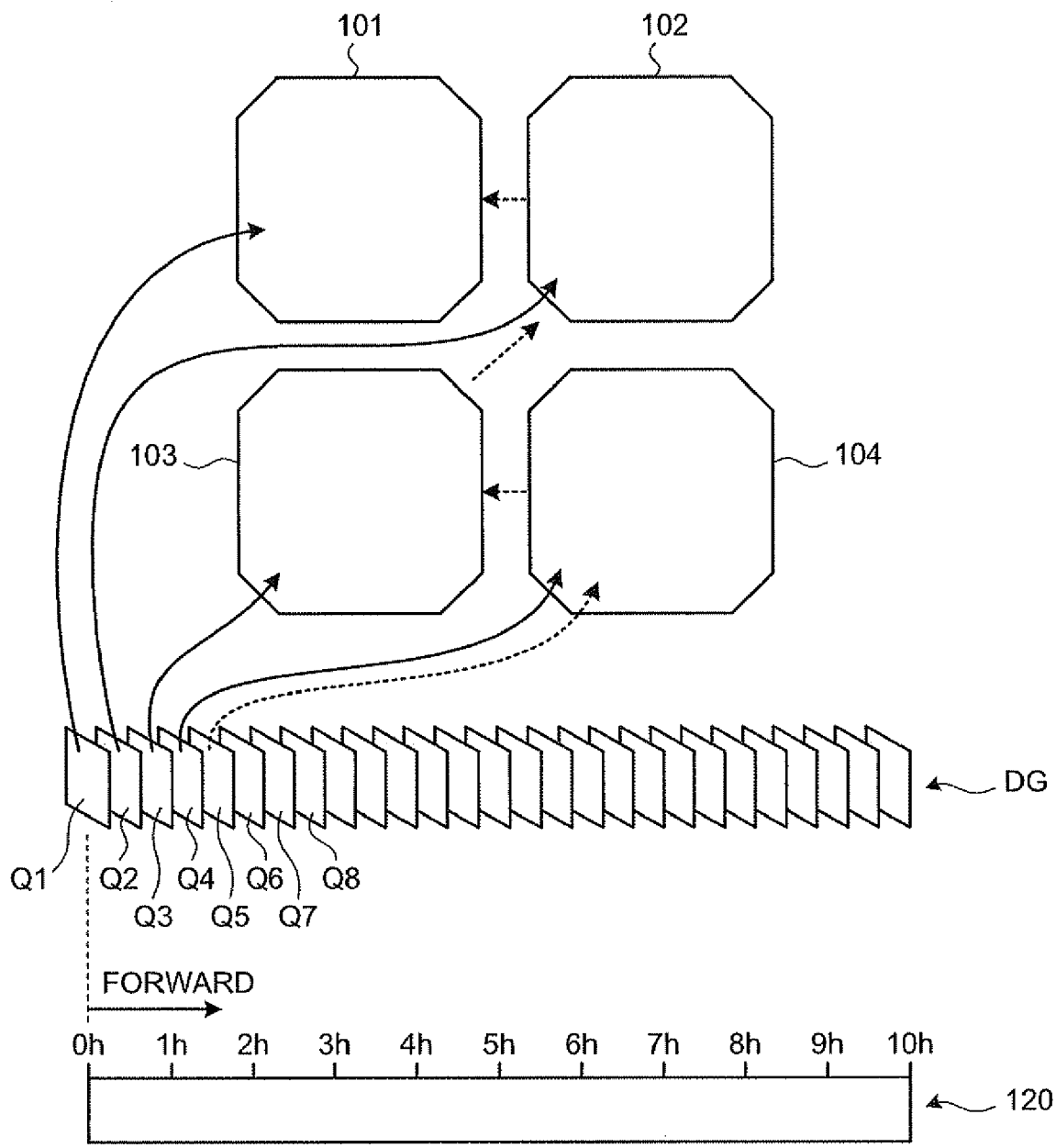
FIG. 12 is a schematic diagram for explaining the action for sequentially switching and displaying the four images in another switching order 3.

The display controller 15b may switch the four continuous images 101 to 104 of the image group DG so as to shift frame by frame in time sequence. FIG. 12 is a schematic diagram for explaining the action for sequentially switching and displaying the four images 101 to 104 in another switching order 3.

In this case, as shown in FIG. 12, the display controller 15b performs control over the display unit 12 so as to display the four continuous images Q1 to Q4 of the image group DG as the images 101 to 104 respectively, as in the above-described case of FIG. 11. Next, when causing the display unit 12 to display the image Q5 following the image Q4, the display controller 15b switches the image Q1 of the image 101 to the image Q2 so that the image Q2 being displayed as the image 102 shifts to the image 101, switches the image Q2 of the image 102 to the image Q3 so that the image Q3 being displayed as the image 103 shifts to the image 102, and switches the image Q3 of the image 103 to the image Q4 so that the image Q4 being displayed as the image 104 shifts to the image 103. At the same time, the display controller 15*b* switches the images 104 from the image Q4 to the image Q5. Then, the display controller 15*b* repeats the switching processing of the image display of shifting the images frame by frame for the remaining image group sequentially following the image Q5. This allows the display unit 12 to array and display the four continuous images of the image group DG in the order of the images 101 to 104, and to sequentially switch and display the images 101 to 104 so that they shift frame by frame.

Figure 13:
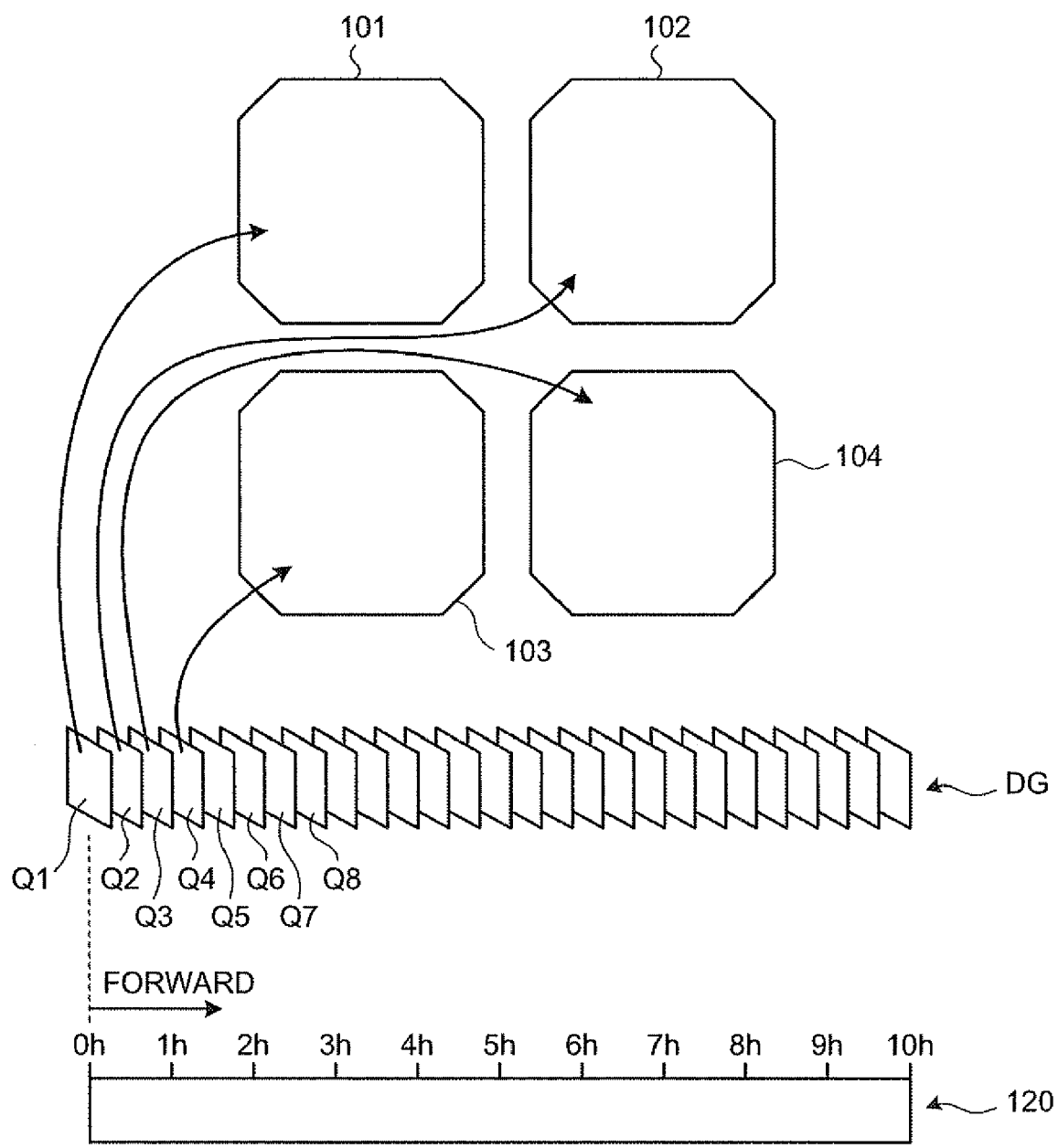
FIG. 13 is a schematic diagram for explaining the action for sequentially switching and displaying the four images in another switching order 4.

Moreover, the display controller 15*b* may perform control over the display unit 12 so as to display the four continuous images of the image group DG in such a manner that they are arrayed in a clockwise order on the screen, for example, in the order of the image 101, image 102, image 104, and image 103. FIG. 13 is a schematic diagram for explaining the action for sequentially switching and displaying the four images 101 to 104 in another switching order 4.

As shown in FIG. 13, the display controller 15*b* first performs control over the display unit 12 so as to display the leading image Q1 of the image group DG as the image 101, and to display the subsequent images Q2 to Q4 as the images 102, 104, 103, respectively. Next, when the display controller 15*b* causes the display unit 12 to display the images Q5 to Q8 sequentially following the image Q4, the display controller 15*b* performs control over the display unit 12 so as to switch the image Q1 to Q4 being displayed as the images 101, 102, 104, 103 to the images Q5 to Q8 and to display them, respectively. Then, the display controller 15*b* repeats the switching processing of the image display for the remaining image group sequentially following the image Q8. This allows the display unit 12 to sequentially switch and display the image group DG four by four so that the four continuous images of the image group DG are arrayed in the clockwise order on the screen, for example, in the order of the images 101, 102, 104, 103.

Figure 14:
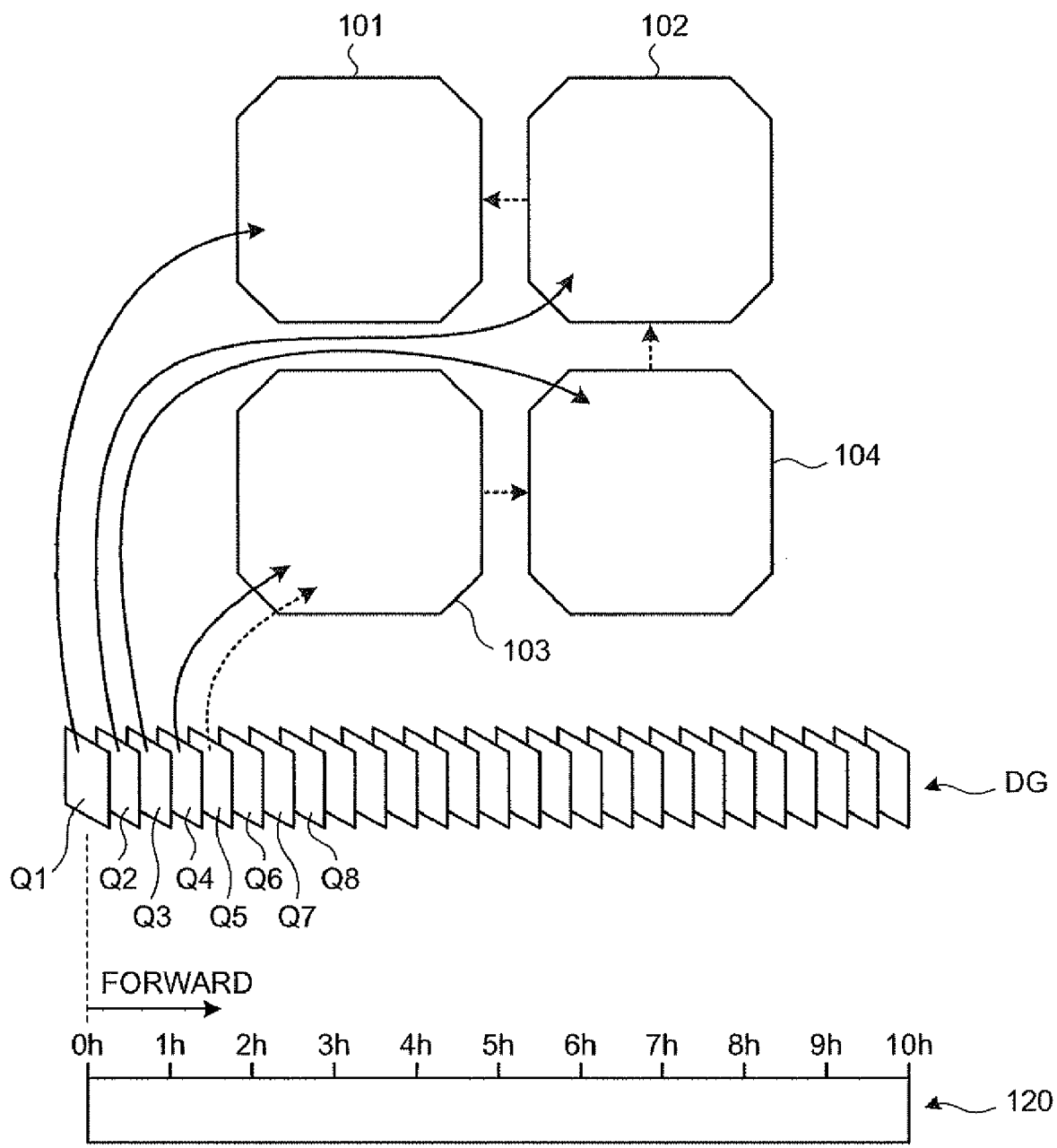
FIG. 14 is a schematic diagram for explaining the action for sequentially switching and displaying the four images in another switching order 5.

The display controller 15*b* may switch the four continuous images 101, 102, 104, 103 of the image group DG so that they shift frame by frame in time sequence. FIG. 14 is a schematic diagram for explaining the action for sequentially switching and displaying the four images 101 to 104 in another switching order 5.

In this case, as shown in FIG. 14, the display controller 15*b* first performs control over the display unit 12 so as to display the four continuous images Q1 to Q4 of the image group DG as the images 101, 102, 104, 103 respectively, as in the above-described case of FIG. 13. Next, when causing the display unit 12 to display the image Q5 following the image Q4, the display controller 15*b* switches the image Q1 of the image 101 to the image Q2 so that the image Q2 being displayed as the image 102 shifts to the image 101, switches the image Q2 of the image 102 to the image Q3 so that the image Q3 being displayed as the image 104 shifts to the image 102, and switches the image Q3 of the image 104 to the image Q4 so that the image Q4 being displayed as the image 103 shifts to the image 104. At the same time, the display controller 15*b* switches the image 103 from the image Q4 to the image Q5. Then, the display controller 15*b* repeats the switching processing of the image display of shifting the images frame by frame for the remaining image group sequentially following the image Q5. This allows the display unit 12 to array and display the four continuous images of the image group DG in the order of the images 101, 102, 104, 103, and to sequentially switch and display the images 101, 102, 104, 103 so that they shift frame by frame.

The display controller 15*b* may perform control over the display unit 12 so as to display the four continuous images of the image group DG in such a manner that they are arrayed in a counterclockwise order on the screen. The control of the display controller 15*b* allows the display unit 12 to array and display the four continuous images of the image group DG in the counterclockwise order on the screen, for example, in the order of the images 102, 101, 103, and 104, and to sequentially switch and display the images 102, 101, 103, 104 four by four or in such a manner that they shift frame by frame.

Figure 15:
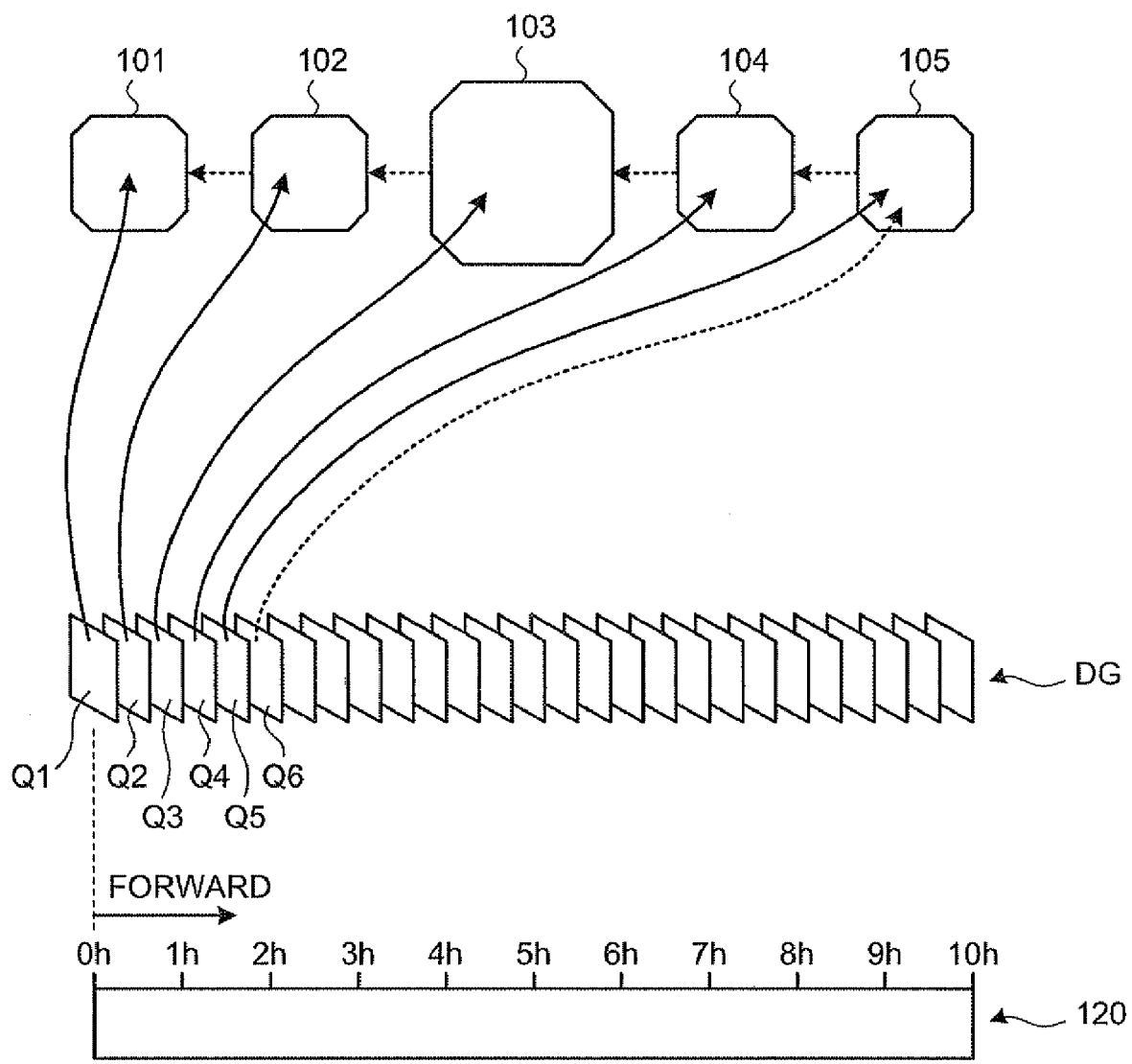
FIG. 15 is a schematic diagram for explaining the action of displaying three or more continuous images in horizontal alignment.

On the other hand, three or more continuous images of the series of image to be displayed may be displayed in horizontal alignment in the main-image display area 100 of the display unit 12 on the screen. FIG. 15 is a schematic diagram for explaining the action of displaying the three or more continuous images in horizontal alignment in the main-image display area 100. As shown in FIG. 15, the display controller 15*b* performs control over the display unit 12 so as to display the series of images to be displayed, for example, the five continuous images Q1 to Q5 of the image group DG as the images 101 to 105 of the main-image display area 100, respectively. In this case, the display unit 12, for example, displays the image 103 as a main image in such a manner as to be larger than any other. At the same time, the display unit 12 displays the continuous images 101, 102 temporally before the image 103, and the continuous images 104, 105 temporally after the image 103 as complementary images showing the regions before and after the image 103.

Moreover, when causing the display unit 12 to display the image Q6 following the image Q5 in the main-image display area 100, the display controller 15*b* switches the image Q1 of the image 101 to the image Q2 so that the image Q2 being displayed as the image 102 shifts to the image 101, switches the image Q2 of the image 102 to the image Q3 so that the image Q3 being displayed as the image 103 shifts to the image 102. Furthermore, the display controller 15*b* switches the image Q3 of the image 103 to the image Q4 so that the image Q4 being displayed as the image 104 shifts to the image 103, and switches the image Q4 of the image 104 to the image Q5 so that the image Q5 being displayed as the image 105 shifts to the image 104. At the same time, the display controller 15*b* switches the images 105 from the image Q5 to the image Q6. Then, the display controller 15*b* repeats the switching processing of the image display of shifting the images frame by frame for the remaining image group sequentially following the image Q6. This allows the display unit 12 to sequentially switch and display the three or more continuous images of the image group DG horizontally on the screen.

Here, the display controller 15*b* only needs to perform control over the display unit 12 so as to display the three or more continuous images in horizontal alignment. In this case, the display unit 12 may display only one piece of the continuous images temporally before the image 103 displayed as the main image, or may display a plurality of pieces. At the same time, the display unit 12 may display only one piece of the continuous images temporally after this image 103, or may display a plurality of pieces.

Figure 16:
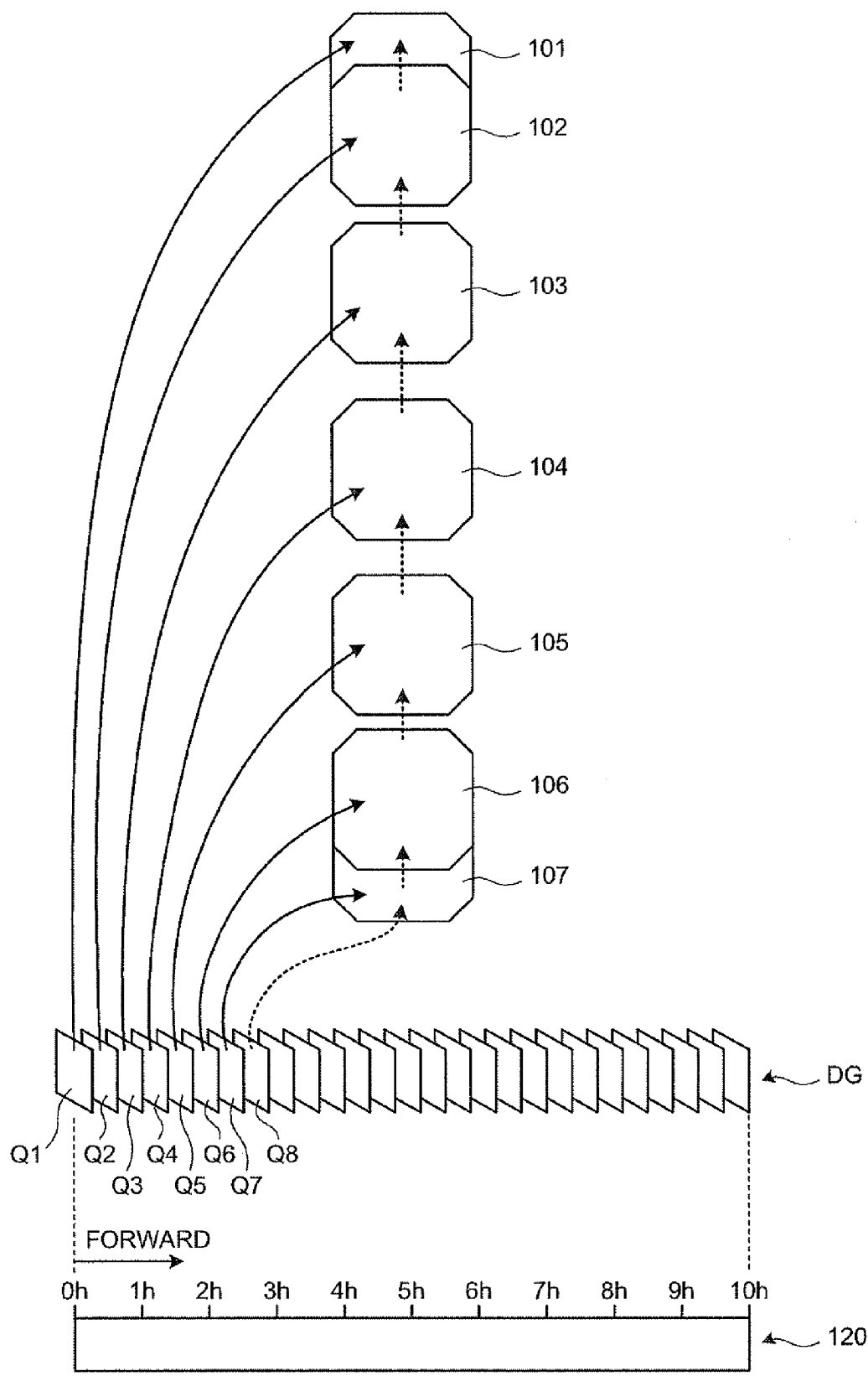
FIG. 16 is a schematic diagram for explaining the action of displaying three or more continuous images in vertical alignment.

Moreover, in the main-image display area 100 of the display unit 12, three or more continuous images of the series of images to be displayed may be displayed in vertical alignment on the screen. FIG. 16 is a schematic diagram for explaining the action of displaying the three or more continuous images in vertical alignment in the main-image display area 100. As shown in FIG. 16, the display controller 15*b* performs control over the display unit 12 so as to display the series of images to be displayed, for example, the seven continuous images Q1 to Q7 of the image group DG as the images 101 to 107 of the main-image display area 100, respectively.

In this case, the display unit 12, for example, displays the image 104 as a main image, and displays the continuous images 101 to 103 temporally before the image 104, and the continuous images 105 to 107 temporally after the image 104 as complementary images showing the regions before and after the image 104. The display unit 12 displays the image 101, which is the farthest from the main image 104 of the temporally previous images, in a state of overlapping the next image 102. Similarly, the display unit 12 displays the image 107, which is the farthest from the main image 104 of the temporally subsequent images, in a state of overlapping the immediately previous image 106. This can promote downsizing of the main-image display area 100 formed for displaying the images 101 to 107, and prevent an occupying percentage of the main-image display area 100 on the display screen of the display unit 12 from excessively increasing.

Moreover, when causing the display unit 12 to display the image Q8 following the image Q7 in the main-image display area 100, the display controller 15b switches the image Q1 of the image 101 to the image Q2 so that the image Q2 being displayed as the image 102 shifts to the image 101, switches the image Q2 of the image 102 to the image Q3 so that the image Q3 being displayed as the image 103 shifts to the image 102, and switches the image Q3 of the image 103 to the image Q4 so that the image Q4 being displayed as the image 104 shifts to the image 103. Furthermore, the display controller 15b switches the image Q4 of the image 104 to the image Q5 so that the image Q5 being displayed as the image 105 shifts to the image 104, switches the image Q5 of the image 105 to the image Q1 so that the image Q6 being displayed as the image 106 shifts to the image 105, and switches the image Q6 of the image 106 to the image Q7 so that the image Q7 being displayed as the image 107 shifts to the image 106. At the same time, the display controller 15b switches the images 107 from the image Q7 to the image Q8. Then, the display controller 15b repeats the switching processing of the image display of shifting the images frame by frame for the remaining image group sequentially following the image Q8. This allows the display unit 12 to sequentially switch and display the three or more continuous images of the image group DG vertically on the screen.

Here, the display controller 15b only needs to perform the control over the display unit 12 so as to display the three or more continuous images in vertical alignment. In this case, the display unit 12 may display only one piece of the continuous images temporally before the image 104 displayed as the main image, or may display a plurality of pieces. At the same time, the display unit 12 may display only one piece of the continuous images temporally after this image 104, or may display a plurality of pieces.

Figure 17:
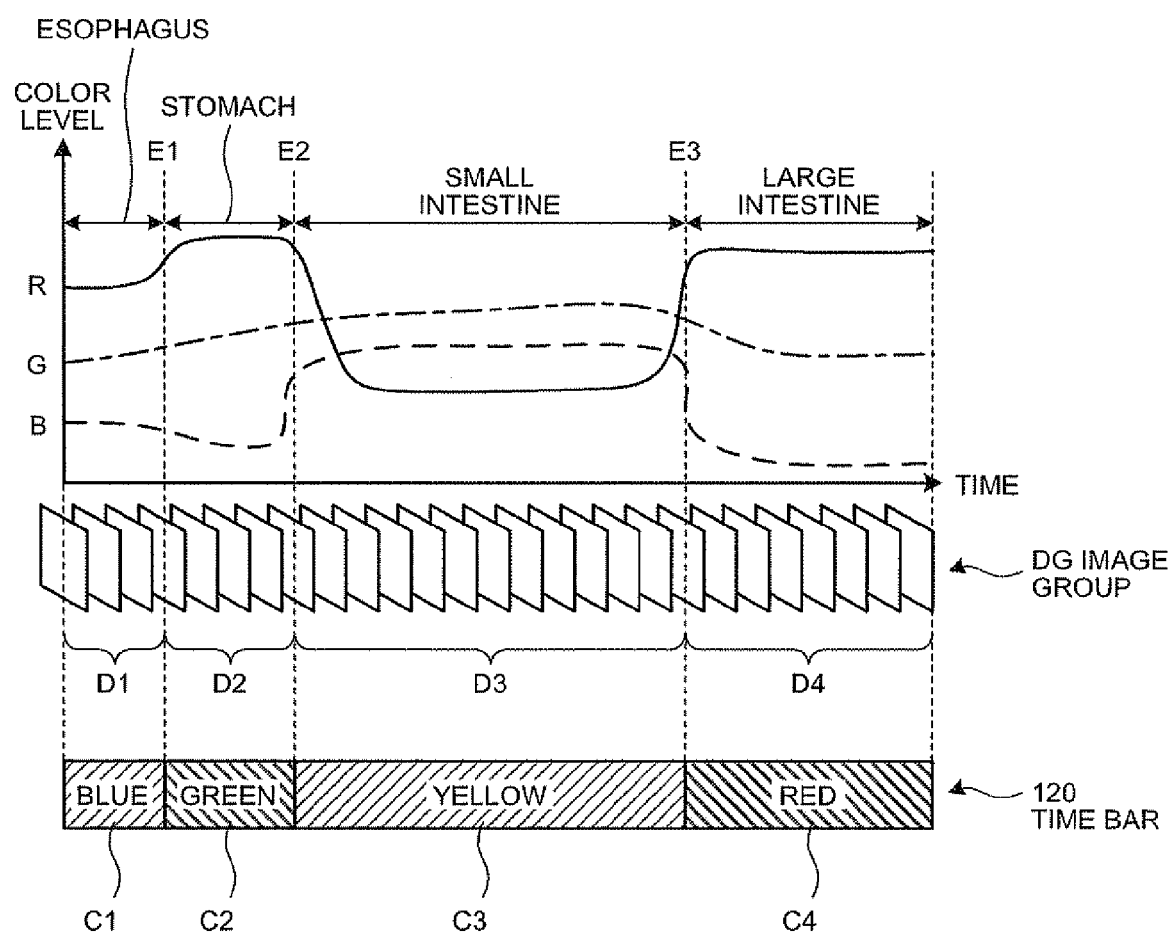
FIG. 17 is a schematic diagram for specifically explaining the action of color-coding the time bar by the observation region of each image determined based on level change in color elements.

While in this embodiment of the invention, the observation region of each of the images contained in the image group to be displayed is determined based on the average color of the image, this invention is not limited to this, but the observation region of each of the images may be determined based on level change in the color elements R, G, B forming the average color of each of the image contained in the image group to be displayed. In this case, the region determining unit 15a detects the color elements R, G, B forming the average color of each of the images of the image group to be displayed as the color information instead of the above-described average color of the relevant image, and determines the observation region of the image based on the level change in the color elements R, G, B. FIG. 17 is a schematic diagram for specifically explaining the action of color-coding the time bar 120 by the observation region of each of the images based on the level change in the color elements R, G, B.

As shown in FIG. 17, the region determining unit 15a repeats the above-described step S103 to detect the color elements R, G, B forming the average colors of the respective images contained in the image group DG to be displayed and detect the level change in the color elements R, G, B of the respective images. In this case, the region determining unit 15a detects the level change in the color elements R, G, B as shown in FIG. 17, for example, with respect to the respective images of the screen group DG.

Here, in the image group DG obtained by sequentially picking up the images of esophagus, stomach, small intestine, and large intestine inside the subject 1 in time sequence, the color levels of the color elements R, G, B of the respective images contained in the image group DG remarkably change, for example, between the images shifting from esophagus to stomach, between the images shifting from stomach to small intestine, and between the images shifting from small intestine to large intestine. Accordingly, by sequentially detecting the remarkable change in the color levels of the color elements R, G, B (particularly, color elements R, B) in time sequence, the region determining unit 15a determines the observation regions of the respective images of the image group DG.

More specifically, the region determining unit 15a sequentially detects edges E1, E2, E3 indicating level changes of the color elements R, G, B, particularly remarkable level changes in the color element R, B in time sequence, and determines that the observation region of the image group D1 until the first edge E1 is detected is esophagus, determines that the observation region of the image group D2 from the detection of the edge E1 to the detection of the next edge E2 is stomach, determines that the observation region of the image group D3 from the detection of the edge E2 to the detection of the next edge E3 is small intestine, and determines that the observation region of the image group D4 after the detection of the edge E3 is large intestine. In this case, the display controller 15b can color-code the time bar 120 by the observation region using the substitute colors C1 to C4 as in the above-described case where the observation region is determined based on the average color of each of the images.

Figure 18:
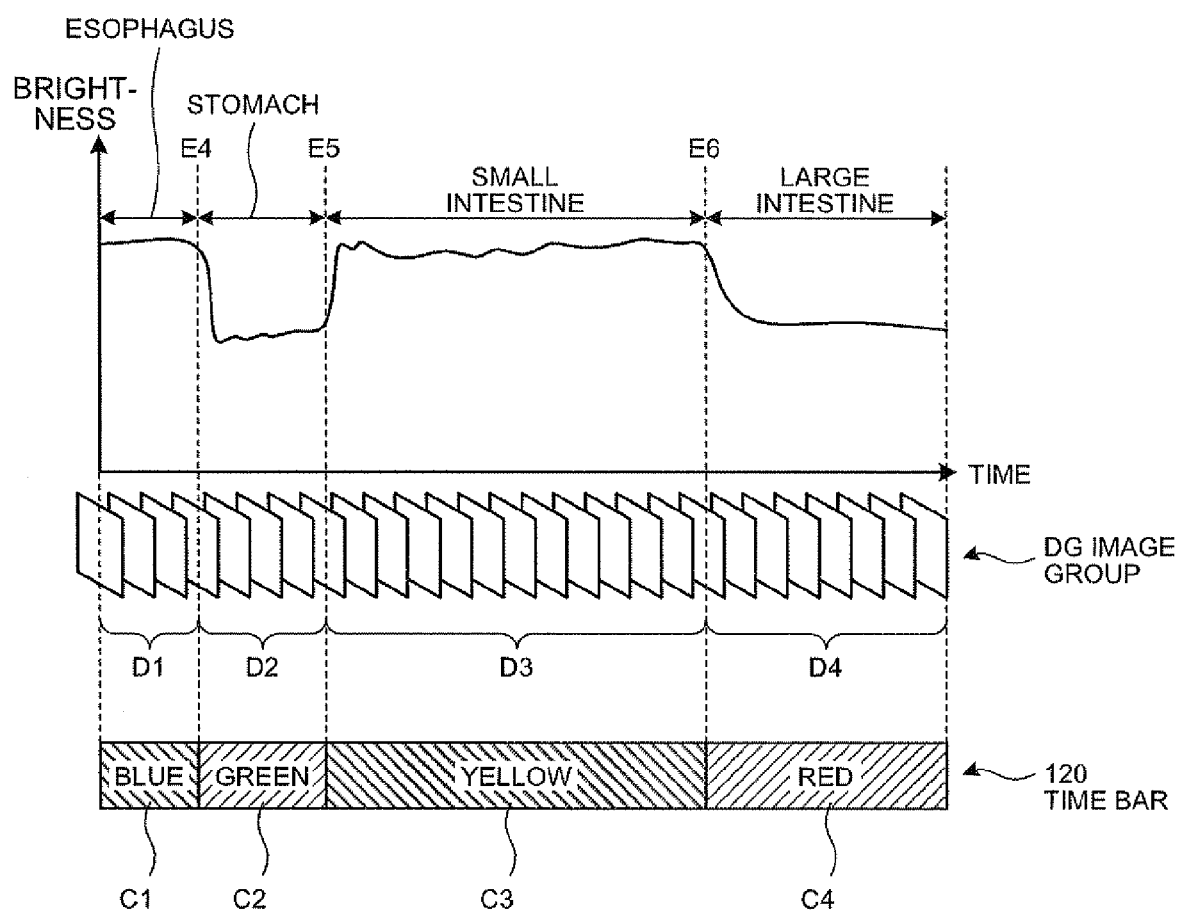
FIG. 18 is a schematic diagram for specifically explaining the action of color-coding the time bar by the observation region of each image determined based on level change in brightness.

On the other hand, while in this embodiment of the invention, the observation region of each of the images contained in the image group to be displayed is determined based on the color information of the image, for example, the average color, this invention is not limited to this, but the observation region of each of the images may be determined based on brightness information of each of the images contained in the image group to be displayed, for example, level change in brightness of the image. In this case, the region determining unit 15a detects brightness Y of each of the images of the image group to be displayed instead of the above-described average color of the image, and determines the observation region of the relevant image based on the level change in the brightness Y. FIG. 18 is a schematic diagram for specifically explaining the action of color-coding the time bar 120 by the observation region of each of the images determined based on the level change in the brightness Y.

As shown in FIG. 18, the region determining unit 15a repeats the above-described step S103 to detect the brightness Y of the respective images contained in the image group DG to be displayed, and detects level change in the brightness Y of the respective images. The brightness Y can be calculated by the following formula (1) using the color elements R, G, B of an image.

Brightness $Y=0.299 \times \text{color element } R + 0.587 \times \text{color element } G + 0.114 \times \text{color element } B$     (1)

The region determining unit 15a detects the color elements R, G, B of the image, calculates the brightness Y of this image by the formula (1), and repeats the operation processing for the respective images of the image group DG to detect the brightness Y of the respective images of the image group DG. In this case, the region determining 15a detects the level change in the brightness Y as shown in FIG. 18, for example, with respect to the respective images of the image group DG.

Here, the brightness Y is a parameter calculated based on the color elements R, G, B as shown in formula (1). The level of the brightness Y, therefore, changes with the level change in the color elements R, G, B by the shift of the observation region in the image group DG. Accordingly, in the image group DG obtained by sequentially picking up the images of esophagus, stomach, small intestine, and large intestine inside the subject 1, the level of the brightness Y of the respective images contained in the image group DG remarkably changes, for example between the images shifting from esophagus to stomach, between the images shifting from stomach to small intestine, and between the images shifting from small intestine to large intestine. Namely, by sequentially detecting the remarkable level change in the brightness Y in time sequence, the region determining unit 15a can determine the observation region of each of the images of the image group DG.

More specifically, the region determining unit 15a sequentially detects edges E4, E5, E6 indicating remarkable level changes in the brightness Y in time sequence, and determines that the observation region of the image group D1 until the first edge E4 is detected is esophagus, determines that the observation region of the image group D2 from the detection of the edge E4 to the detection of the next edge E5 is stomach, determines that the observation region of the image group D3 from the detection of the edge E5 to the detection of the next edge E6 is small intestine, and determines that the observation region of the image group D4 after the detection of the edge E6 is large intestine. In this case, the display controller 15b can color-code the time bar 120 by the observation region using the substitute colors C1 to C4 as in the above-described case where the observation region is determined based on the average color of each of the images.

While in the embodiments of this invention, the observation region is determined for all the images contained in the series of images to be displayed, respectively, this invention is not limited to this, but a desired number of frames of the images contained in the series of images to be displayed may be thinned out and the observation region may be determined for each of the remaining images of the image group.

Moreover, while in the embodiments of this invention, spectral colors such as blue, green, yellow, and red are used as the substitute colors corresponding to the respective observation regions, this invention is not limited to this, but as the substitute colors corresponding to the respective observation regions, desired colors may be used as long as they have enough contrast to form the border with the adjacent substitute color when displayed on the time bar 120.

As described above, in the embodiments of this invention, the observation region of each the images contained in the series of images obtained by imaging the inside of the subject is determined, the substitute color corresponding to the observation region is displayed in the area on the time bar temporally corresponding to the relevant image to color-code the time bar by the observation region, and as the substitute colors, those having enough contrast to form the color border when they are adjacent to each other on the time bar are used. Therefore, by forming the border of the substitute colors on the time bar, the border of the images when the observation region displayed on the series of images to be displayed change can be shown clearly, which brings about an effect of realizing the image display apparatus capable of easily determining intra-subject observation regions whose images are displayed.

By visually confirming the substitute color and the border on the time bar, the examiner such as a doctor and a nurse can easily determine the intra-subject observation region whose image is displayed, and knows whether or not the observation region has changed to another observation region before and after the relevant image, for example, whether or not the observation region has shifted from esophagus to stomach.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus comprising:
   a display unit that displays a series of images obtained by imaging an inside of a subject in time sequence, and displays a time bar indicating imaging periods of the series of images so that areas of the time bar are identified by different colors corresponding respectively to regions of the inside of the subject; and
   a control unit that identifies the respective regions of the inside of the subject, which are displayed on the series of images, and controls the display unit so that, for each of the regions identified, an area of the time bar corresponding to a period when a series of images of the region are displayed is colored with a substitute color identifying the region,
   wherein the control unit detects color information of each of the series of images to identify the respective regions of the inside of the subject based on the color information,
   the substitute color coloring the area is determined independently of the detected color information, and
   the substitute color has contrast to form a border with an adjacent substitute color on the time bar.

2. The image display apparatus according to claim 1, wherein the substitute color is a spectral color.

3. The image display apparatus according to claim 1, wherein the control unit calculates brightness information of each of the series of images based on the detected color information to identify the respective regions of the inside of the subject based on said brightness information.

4. The image display apparatus according to claim 1, wherein the control unit controls the display unit so that an index is displayed on the time bar, the index indicating a position where a currently-displayed image is on the time bar.

5. The image display apparatus according to claim 1, wherein
   the control unit calculates an average color of each of the series of images based on the detected color information to identify the respective regions of the inside of the subject based on the average color, and
   the substitute color coloring the area is different from the average color of the corresponding region.

* * * * *